(12) United States Patent
Okamura et al.

(10) Patent No.: US 9,005,383 B2
(45) Date of Patent: *Apr. 14, 2015

(54) METHOD FOR MANUFACTURING CERAMIC MEMBER, AND CERAMIC MEMBER, GAS SENSOR DEVICE, FUEL CELL DEVICE, MULTI-LAYER PIEZOELECTRIC DEVICE, INJECTION APPARATUS AND FUEL INJECTION SYSTEM

(71) Applicant: Kyocera Corporation, Kyoto-shi, Kyoto (JP)

(72) Inventors: Takeshi Okamura, Aira (JP); Tomohiro Kawamoto, Kirishima (JP); Shigenobu Nakamura, Kirishima (JP)

(73) Assignee: Kyocera Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,896

(22) Filed: Feb. 26, 2013

(65) Prior Publication Data

US 2013/0183187 A1 Jul. 18, 2013

Related U.S. Application Data

(62) Division of application No. 12/281,763, filed as application No. PCT/JP2007/053768 on Feb. 28, 2007, now abandoned.

(30) Foreign Application Priority Data

| Mar. 7, 2006 | (JP) | 2006-061351 |
| Aug. 29, 2006 | (JP) | 2006-232019 |
| Oct. 27, 2006 | (JP) | 2006-293211 |

(51) Int. Cl.
*C03B 29/00* (2006.01)
*B22F 7/08* (2006.01)
(Continued)

(52) U.S. Cl.
CPC .............. *B22F 7/08* (2013.01); *G01N 27/4073* (2013.01); *H01L 41/0471* (2013.01);
(Continued)

(58) Field of Classification Search
CPC .............. B22F 7/08; B32B 3/26; C04B 35/64
USPC ........................ 156/89.12, 89.11, 89.17; 419/9
See application file for complete search history.

(56) References Cited

U.S. PATENT DOCUMENTS

| 6,344,118 B1 | 2/2002 | Kobayashi et al. ........... 204/424 |
| 7,554,251 B2 * | 6/2009 | Kondo et al. ................. 310/366 |

(Continued)

FOREIGN PATENT DOCUMENTS

| EP | 1898476 | 3/2008 |
| JP | 03-064979 | 3/1991 |

(Continued)

*Primary Examiner* — Alex Efta
(74) *Attorney, Agent, or Firm* — Volpe and Koenig, P.C.

(57) ABSTRACT

A ceramic member in which the metal layers with high void ratio are sufficiently sintered to lower a residue of resin is produced.
The method for manufacturing a ceramic member which comprises a step of forming a stacked compact from a plurality of metallic paste layers containing a metal component $M_1$ that are stacked one on another via ceramic green sheets, and a step of firing the stacked compact, wherein at least one of plural metallic paste layers is formed as a second metallic paste layer that has the mass percentage X higher than that of the metallic paste layer that adjoin therewith in the stacking direction, the mass percentage X being the proportion of the metal component $M_1$ to the total metal content in the metallic paste layer.

18 Claims, 19 Drawing Sheets

(51) Int. Cl.
   *G01N 27/407* (2006.01)
   *H01L 41/047* (2006.01)
   *H01L 41/083* (2006.01)
   *H01L 41/273* (2013.01)
   *H01M 8/12* (2006.01)

(52) U.S. Cl.
   CPC ....... *H01L 41/0477* (2013.01); *H01L 41/0838* (2013.01); *H01L 41/273* (2013.01); *H01M 8/1246* (2013.01); *Y02E 60/521* (2013.01); *Y02E 60/525* (2013.01)

(56) References Cited

U.S. PATENT DOCUMENTS

| | | | |
|---|---|---|---|
| 7,936,108 B2 | 5/2011 | Nakamura | 310/328 |
| 2004/0166386 A1 | 8/2004 | Herman et al. | 429/22 |
| 2006/0181178 A1* | 8/2006 | Kastl et al. | 310/328 |
| 2007/0278907 A1 | 12/2007 | Kondo et al. | 310/364 |
| 2009/0295256 A1 | 12/2009 | Okamura et al. | |

FOREIGN PATENT DOCUMENTS

| | | |
|---|---|---|
| JP | 06-258281 | 9/1994 |
| JP | 06-317555 | 11/1994 |
| JP | 11-051899 | 2/1999 |
| JP | 2000-106461 | 4/2000 |
| JP | 2001-250994 | 9/2001 |
| JP | 2006-013437 | 1/2006 |
| WO | WO 2005/029602 A1 | 3/2005 |
| WO | WO 2005086247 A1 * | 9/2005 |
| WO | WO 2006/000479 A1 | 1/2006 |
| WO | WO 2006000479 A1 * | 1/2006 |

* cited by examiner

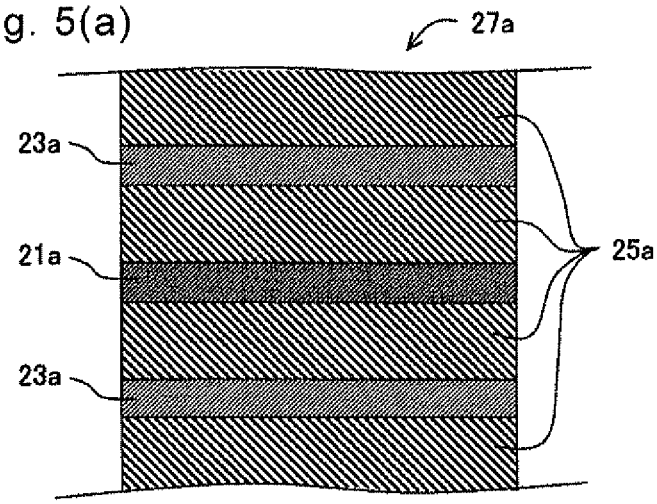
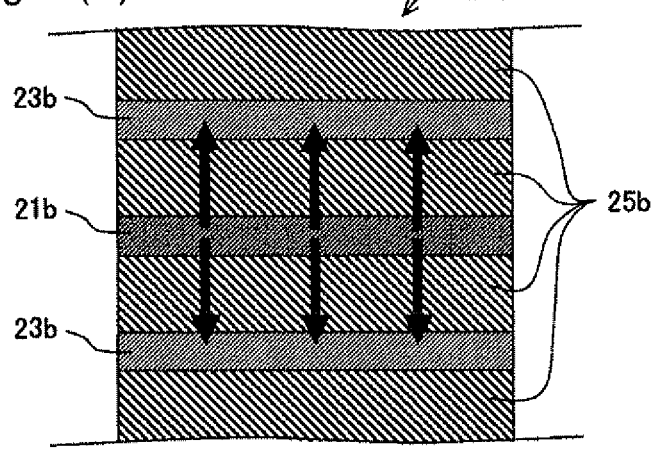
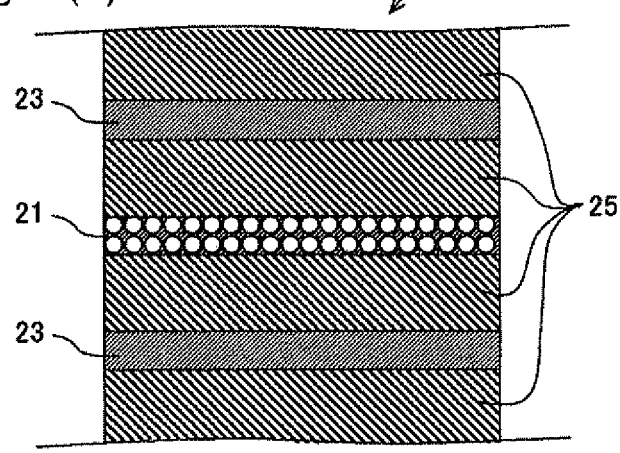

US 9,005,383 B2

METHOD FOR MANUFACTURING CERAMIC MEMBER, AND CERAMIC MEMBER, GAS SENSOR DEVICE, FUEL CELL DEVICE, MULTI-LAYER PIEZOELECTRIC DEVICE, INJECTION APPARATUS AND FUEL INJECTION SYSTEM

TECHNICAL FIELD

The present invention relates to a method for manufacturing a ceramic member, and the ceramic member manufactured thereby. More particularly, the present invention relates to a gas sensor device used in, for example, monitoring indoor atmosphere, atmosphere in a cave or tunnel and exhaust gas, a fuel cell device used in power generation or the like and a multi-layer piezoelectric device to be used in a fuel injection system of automobile engine, a micro movement drive apparatus, a piezoelectric sensor device, a piezoelectric circuit, etc., and methods for manufacturing the same.

BACKGROUND ART

The gas sensor device and the fuel cell device have functions to bring a gas into contact with the ceramic members that constitute these devices, so as to have particular component of the gas adsorbed onto the ceramic surface or permeate therethrough. To provide this function, such attempts have been made as forming metal layers (electrodes) in a highly porous structure so as to increase gas permeability, or controlling the surface area covered by an electrode by forming the electrode in comb or other shape in case the electrode is dense (refer to, for example, Japanese Unexamined Patent Publication (Kokai) No. 6-317555 and Japanese Unexamined Patent Publication (Kokai) No. 6-258281).

A metal layer having a high void ratio can be manufactured by, for example, forming an electrode by printing a metal that can be sintered only at temperatures higher than the sintering temperature of ceramics, and firing the ceramics and the electrode metal at the same time.

There is also such a method as an electrode paste prepared by mixing a metal powder and a ceramics powder that cannot be sintered at the sintering temperature of the electrode metal is printed and fired. Other methods of forming a metal layer having a high void ratio include firing of Pt electrode described in Japanese Unexamined Patent Publication (Kokai) No. 11-51899.

DISCLOSURE OF THE INVENTION

With the prior art method of forming the metal layer having a high void ratio, there have been such cases as sintering of the electrode does not proceed sufficiently while the ceramics is sintered sufficiently during simultaneous firing. There may also be such a case as a component having low electrical conductivity existing in the metallic grain boundaries decreases the electrical conductivity that is the critical property of the electrode, with the higher resistance of the electrode resulting in a lower sensitivity of the electrical signal propagating through the electrode. This makes it necessary to increase the drive voltage, which causes the device to consume more electricity.

A method for manufacturing a typical ceramic member of the present invention comprises the steps of forming a stacked compact from plural metallic paste layers containing a metal component $M_1$ that are stacked one on another via ceramic green sheets, and firing the stacked compact, wherein at least one of plural metallic paste layers is formed as a second metallic paste layer that has a mass percentage X higher than that of a first metallic paste layer that adjoins therewith in the stacking direction in the step of forming the stacked compact, the mass percentage X being the proportion of the metal component $M_1$ to the total metal content in the metallic paste layer.

In a typical method for manufacturing a ceramic member of the present invention, at least one of plural metallic paste layers is formed as the second metallic paste layer that has a higher mass percentage X than that of the first metallic paste layer that adjoins therewith in the stacking direction. As the stacked compact is fired with the mass percentage X of the metal component $M_1$ differentiated (rendered a concentration gradient) between the metallic paste layers that adjoin via the ceramic green sheet, it is made possible to cause the metal component $M_1$ to diffuse through the ceramic layer from a layer having a higher mass percentage X to a layer having lower mass percentage X. Since the metal layer formed by sintering the second metallic paste layer shrinks in volume as the metal component $M_1$ diffuses, a void ratio of the second metal layer increases. Thus the manufacturing method of the present invention makes it possible to manufacture the ceramic member having the metal layers that include many voids by firing the stacked compact having such a constitution as the mass percentage X of the metal component $M_1$ is differentiated between the first metallic paste layer and the second metallic paste layer that adjoin each other via the ceramic green sheet.

BRIEF DESCRIPTION OF THE DRAWINGS

FIG. 5(a) to FIG. 5(c) are schematic diagrams showing a method of manufacturing the ceramic member according to the embodiment shown in FIG. 4.

11 Second metal layer, 11$a$ Second metallic paste layer, 13 First metal layer, 13$a$ First metallic paste layer, 15 Ceramic layer, 15$a$ Ceramic green sheet, 17 Ceramic member, 17$a$ Stacked perform.

BEST MODE FOR CARRYING OUT THE INVENTION

Figure 1:
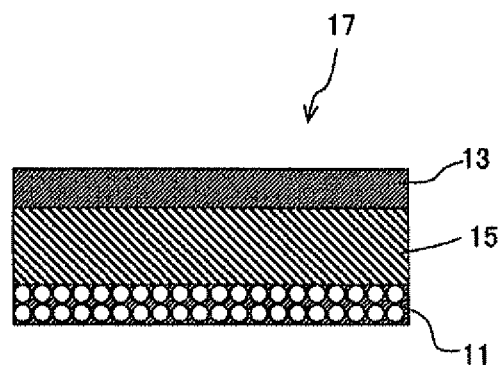
FIG. 1 is a sectional view showing one embodiment of a ceramic member that has the most basic constitution of the present invention.

A ceramic member according to one embodiment of the present invention and a method for manufacturing the same will now be described in detail. FIG. 1 is a sectional view showing one embodiment of ceramic member 17 that has the most basic constitution of the present invention. As shown in FIG. 1, the ceramic member 17 is formed by stacking two metal layers (first metal layer 13 and second metal layer 11) via a ceramic layer 15.

Figure 12:
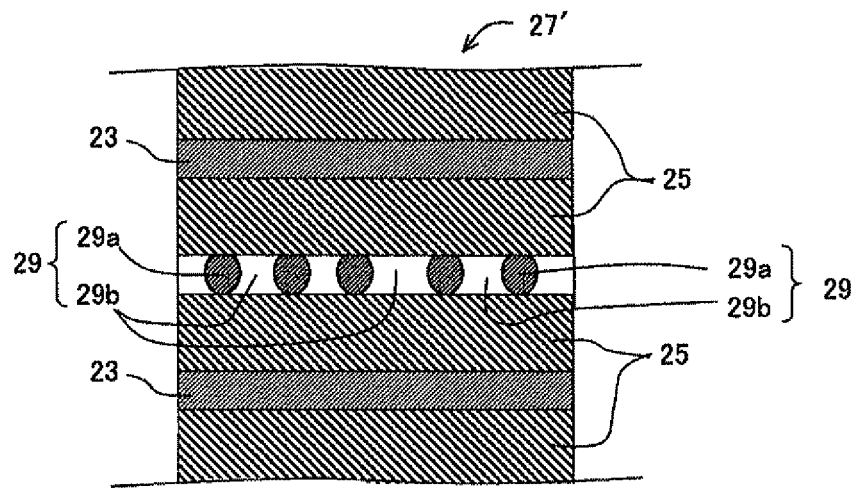
FIG. 12 is a sectional view showing a ceramic member according to further another embodiment of the present invention.

The second metal layer 11 has more voids than the first metal layer 13 that adjoin therewith in the stacking direction. The second metal layer 11 may be a porous layer having plural independent bubbles therein, or may be constituted from plural metal lumps that are separated from by voids as shown in FIG. 12 and described later. Hereafter the second metal layer 11 having these forms will be collectively called porous metal layer 11. In the present invention, the word "void" refers to a gap formed in the metal layer. Specifically, in the case of a porous layer, the void refers to the bubble described above and, in the case of constitution formed from plural metal lumps, the void refers to the gap formed between the metal lumps.

The ceramic member 17 has a three-layer structure comprising a metal layer 13 (first metal layer 13) containing a metal component $M_1$, a porous metal layer 11 (second metal layer 11) that includes more voids than the metal layers 13 have, and the ceramic layer 15 sandwiched between these metal layers.

Figure 2A:
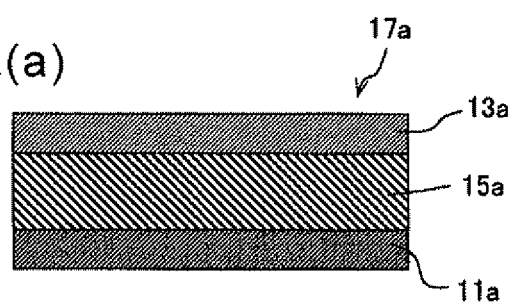
FIG. 2(a) to FIG. 2(c) are schematic diagrams showing a method of manufacturing ceramic member according to one embodiment of the present invention.

A method according to one embodiment of the present invention for manufacturing the ceramic member 17 having the porous metal layer 11 is as follows. FIG. 2($a$) to FIG. 2($c$) are schematic diagrams showing a method of manufacturing ceramic member according to this embodiment. This manufacturing method comprises the steps of forming a stacked compact 17$a$ from metallic paste layers 11$a$, 13$a$ stacked one on another via ceramic green sheets 15$a$, and a firing the stacked compact 17$a$.

As shown in FIG. 2($a$), the stacked compact 17$a$ is formed by stacking the first metallic paste layer 13$a$ and the second metallic paste layer 11$a$ on both principal surfaces of the ceramic green sheet 15$a$. The first metallic paste layer 13$a$ and the second metallic paste layer 11$a$ are disposed at positions that oppose each other in the stacking direction. The first metallic paste layer 13$a$ and the second metallic paste layer 11$a$ include the metal component $M_1$ as the main component.

The second metallic paste layer 11$a$ is prepared so as to have a mass percentage X higher than that of the first metallic paste layer 13$a$ that adjoins therewith in the stacking direction, the mass percentage X being the proportion of the metal component $M_1$ to the total metal content in the metallic paste layer. In the description that follows, the second metallic paste layer 11$a$ may also be referred to as high-content metallic paste layer 11$a$.

The ceramic green sheet 15$a$ is formed as follows. First, a ceramic material powder, a binder made of an organic polymer such as acryl- or butyral-based material and a plasticizer such as DBP (dibutyl phthalate) or DOP (dioctyl phthalate) are mixed to form a slurry. The slurry is formed into a sheet by a tape molding method such as a doctor blade method or a calender roll method, thereby to make the ceramic green sheet 15$a$.

The high-content metallic paste layer 11$a$ and the metallic paste layer 13$a$ are formed as follows. First, a metal powder, an alloy powder or the like is mixed with a binder and a plasticizer to prepare a metallic paste. In this process, the metallic paste used to form the high-content metallic paste layer 11$a$ is prepared so as to have higher mass percentage X of the metal component $M_1$ than the metallic paste used to form the metallic paste layer 13$a$.

Then the metallic pastes prepared as described above are applied onto both principal surfaces of the ceramic green sheet 15$a$ by screen printing technique or the like, to form the high-content metallic paste layer 11$a$ and the metallic paste layer 13$a$ which are then dried. The stacked compact 17$a$ thus formed may be cut into a desired shape as required. The thicknesses of the high-content metallic paste layer 11$a$ and the metallic paste layer 13$a$ are controlled in a range, for example, from 1 to 40 μm.

Two ceramic green sheets are prepared, with the high-content metallic paste layer 11$a$ formed on the principal surface of one sheet and the metallic paste layer 13$a$ formed on the principal surface of another sheet. Then the stacked compact 17$a$ can be made also by placing the two ceramic green sheets one on another so that the principal surfaces thereof where the metallic paste layer is not formed face each other.

Figure 2B:
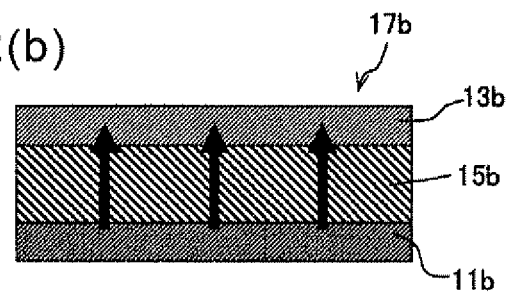
Figure 2C:
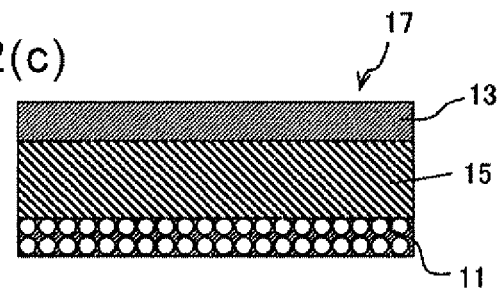

After heating the stacked compact 17a made as described above to a predetermined temperature to remove the binder, the stacked compact 17a is fired at a temperature from about 800 to 1,500° C. FIG. 2(b) shows the stacked compact 17b during firing, and FIG. 2(c) shows the ceramic member 17 after firing. As the stacked compact is fired with the mass percentage X of the metal component $M_1$ differentiated (rendered a concentration gradient) between the metallic paste layers 11a, 13a that adjoin each other via the ceramic green sheet 15a as described above, it is made possible to cause the metal component $M_1$ to diffuse through the ceramic layer from a layer having a higher mass percentage X to a layer having lower mass percentage X.

Thus the metal layer that includes much voids can be formed in a desired place in the ceramic member. Moreover, since the ceramic member allows the sintering of the metal layer to proceed sufficiently without using the acrylic resin unlike in the prior art, there remain extremely small amount of impurities such as resin in the metal layer.

Such diffusion of the metal component $M_1$ is supposed to occur for the following reason. As the metal component $M_1$ is contained in the high-content metallic paste layer 11a formed on the principal surface of one sheet and the metallic paste layer 13a with different values of mass percentage X, the difference in concentration of the metal component $M_1$ becomes the driving force according to the Fick's law to cause the metal component $M_1$ to diffuse from the high-content metallic paste layer to the adjacent metallic paste layer.

The high-content metallic paste layer 11a has at least one of an alloy powder containing the metal component $M_1$ and a metal powder consisting of the metal component $M_1$, added therein. The metallic paste layer 13a that adjoins the high-content metallic paste layer 11a in the stacking direction has at least one of the alloy powder containing the metal component $M_1$ and the metal component $M_2$ and a mixed powder containing a metal powder consisting of the metal component $M_1$ and a metal powder consisting of the metal component $M_2$, added therein. Hereafter the metal powder, the alloy powder and the mixed powder will be collectively referred to as "metal powder and the like".

It is preferable to use such a combination of the metal component $M_1$ and the metal component $M_2$ that causes an alloy to be formed from these metal components. It is more preferable to use such a combination as these metal components do not easily form an intermetallic compound. It is further more preferable to use such a combination that these metal components react totally to form solid solution.

Specifically, it is preferable according to the present invention that the metal component $M_1$ is a Group 11 element of the periodic table and the metal component $M_2$ is a Group 10 element. Since an alloy of a Group 11 element and a Group 10 element reacts totally to form solid solution, an alloy consisting of the component elements in any proportions can be formed, and stable diffusion of the metal components is made possible. Also the alloy has a melting point higher than the sintering temperature of the ceramics, which makes it possible to fire even in an oxidizing atmosphere. Among various alloys, it is preferable to use a silver-platinum alloy or silver-palladium alloy that can be fired simultaneously with ceramics.

It is particularly preferable that the metal component $M_1$ is silver and the metal component $M_2$ is palladium. This is because silver oxide that is generated when silver is heated can form liquid phase of ceramics at a low temperature. As a result, sintering of the ceramics layer 15 can be caused to proceed by containing silver. In addition to the fact that silver and palladium react totally to form solid solution, liquidus and solidus thereof are proximate to each other, so that they can easily form solid solution with each other. Therefore when the silver component diffuses from the porous metal layer 11b that has higher silver concentration into the metal layer 13b via the liquidus, both elements selectively attract each other so as to form an alloy with various compositions. As a result, silver that has lower melting point than palladium diffuses earlier than palladium, and the diffusion proceeds in a shorter period of time (refer to FIG. 2(b)).

The mass percentage X ((metal component $M_1$/total metal content)×100) in the high-content metallic paste layer 11a is preferably in a range of $85 \leq X \leq 100$ so as to stabilize the electrical characteristics of the ceramic member. By controlling the mass percentage X not lower than 85, resistivity of the metal layer can be suppressed from increasing.

In the ceramic members that has been sintered, in order to suppress ion migration of a Group 11 element contained in the metal layer into the ceramic layer, the mass percentage X in the high-content metallic paste layer 11a is more preferably in a range of $85 \leq X \leq 99.999$, and further more preferably in a range of $90 \leq X \leq 99.9$ so as to improve durability of the ceramic member. In order to achieve higher durability, the mass percentage X is more preferably in a range of $90.5 \leq X \leq 99.5$, and further more preferably in a range of $92 \leq X \leq 98$ so as to improve the durability further.

The mass percentage X in the metallic paste layer 13a is preferably in a range of $85 \leq X < 100$ so as to stabilize the electrical characteristics of the ceramic member. In order to suppress ion migration of a Group 11 element contained in the metal layer into the ceramic layer, mass percentage X is more preferably in a range of $85 \leq X \leq 99.999$. The mass percentage X is more preferably in a range of $90 \leq X \leq 99.9$ in order to improve durability of the ceramic member. In order to achieve higher durability, mass percentage X is more preferably in a range of $90.5 \leq X \leq 99.5$, and further more preferably in a range of $92 \leq X \leq 98$ so as to improve the durability further.

The mass percentage X in the high-content metallic paste layer 11a may be set higher than that in the metallic paste layer 13a that adjoins therewith in the stacking direction. There is no restriction on the difference in mass percentage between these layers (mass percentage XH in the high-content metallic paste layer 11a minus mass percentage XL in the metallic paste layer 13a).

In a case where the metal component $M_1$ is silver and the metal component $M_2$ is palladium or platinum, the difference in mass percentage is preferably set as follows. In order to promote diffusion of the metal component $M_1$, the difference in mass percentage is preferably 0.1 or larger.

On the other hand, the difference in mass percentage is preferably not larger than 30, in order to suppress the metal component $M_1$ from excessively diffusing into the metallic paste layer 13a and causing adjacent ceramic layers from joining with each other. Thus the difference in mass percentage is preferably in a range from 0.1 to 30.

When the metal component $M_1$ is slow to diffuse, much metal component $M_1$ may remain in the ceramics at the time when sintering of ceramics in the ceramic green sheet 15a that is adjacent to the high-content metallic paste layer 11a has completed. In order to suppress the metal component $M_1$ from remaining in the ceramics, the difference in mass percentage may be increased so that the metal component $M_1$ diffuses faster. In order to increase the diffusion rate of the metal component $M_1$, the difference in mass percentage is preferably 1 or larger.

When the mass percentage is made different between the high-content metallic paste layer 11a and the metallic paste layer 13a, as mentioned previously, silver diffuses in such a direction as the concentration gradient between the paste layers decreases. When the difference in mass percentage increases to some extent, it is made easier for palladium to diffuse from the metallic paste layer 13a into the high-content metallic paste layer 11a in addition to the diffusion of silver from the high-content metallic paste layer 11a into the metallic paste layer 13a. In order to accelerate the mutual diffusion such as this, the difference in mass percentage is preferably 2 or larger.

When the rate of diffusion of the metal component $M_1$ becomes faster, sintering of the metal layer tends to complete earlier, and the metal layer may be sintered at a temperature lower than the sintering temperature of the ceramic layer. When the liquid phase generated from the metal layer during firing decreases, the density of sintered ceramics tends to become lower. Therefore, in order to control the rate of diffusion of the metal component $M_1$ so as to increase the density of sintered ceramics, the difference in mass percentage is more preferably not larger than 10. Thus the difference in mass percentage is preferably in a range from 1 to 10, and more preferably from 2 to 10.

In order to achieve both the stress relieving effect and the insulating performance at the same time, the difference in mass percentage is particularly preferably in a range from 3 to 5. When the difference in mass percentage is in a range from 3 to 5, silver diffuses to a favorable extent and the second metal layer 11 of such a constitution is obtained after firing that consists of plural metallic lumps separated from each other by voids. The metallic lumps are dispersed between the ceramic layers while being electrically isolated from each other. As a result, the second metal layer 11 becomes a layer of high insulation that does not function as an electrode. Moreover, since plural metallic lumps with proper size and proper quantity are dispersed between the ceramic layers, the ceramic layers on both sides can be prevented from joining together during firing.

As described above, the second metal layer 11 that includes plural metallic lumps dispersed therein achieves the stress relieving function extremely well during operation of the device, when used as the multi-layer piezoelectric device. The second metal layer 11 has lower rigidity than the other portions of the device, and therefore stress tends to concentrate in the second metal layer 11 during operation. The stress tends to concentrate particularly around the interface between plural metallic lumps and the piezoelectric layer. It is supposed that stress is relieved as the piezoelectric material in the interface undergoes localized deformation.

Now let the mass percentage of the metal component $M_2$ in the total metal content in the metallic paste layer be Z. In case the metal component $M_2$ is an element of group 8 to 10 of the periodic table, resistivity of the metal layer can be suppressed from increasing by controlling the mass percentage Z ((mass of metal component $M_2$/total metal content)×100) to 15 or less. This enables it to suppress heat generation from the metal layer when electric current is supplied to the ceramic member. As a result, the ceramic layer that has temperature dependency is suppressed from changing the electrical characteristics thereof under the influence of heat, so as to suppress device characteristics of sensor, fuel cell, multi-layer piezoelectric device or the like from varying during operation.

In case the metal layer is constituted only from a Group 11 element, ion migration tends to occur when used in a highly humid environment over a long period of time, and therefore mass percentage Z is preferably in a range of $0.001 \leq Z \leq 15$. In order to improve durability of the ceramic member, the mass percentage Z is preferably in a range of $0.1 \leq Z \leq 10$. When high heat conductivity and higher durability are required, the mass percentage Z is more preferably in a range of $0.5 \leq Z \leq 9.5$, and is furthermore preferably in a range of $2 \leq Z \leq 8$ if further higher durability is required. Contents (mass) of the metal components $M_1$ and $M_2$ in the metal layer may be determined, for example, by EPMA (Electron Probe Micro Analysis).

When firing is continued long enough to bring diffusion into equivalence, palladium is also enabled to diffuse so that composition of the porous metal layer 11 and composition of the metal layer 13 become proximate to each other. In the ceramic member that has been fired until composition of the lump containing layer 11 and composition of the metal layer 13 become proximate to each other, ion migration of the metal component is suppressed from occurring even when operated at a high temperature, and the electrodes exhibit stable performance.

Silver has a tendency to be bond with palladium. The oxide (silver oxide) is generated when silver is heated at a temperature fairly lower than the melting point of silver, and can form liquid phase together with the component of ceramics. Thus diffusion can be made more likely to occur at a low temperature by adding silver powder to the high-content metallic paste layer 11a and a silver-palladium alloy powder to the metallic paste layer 13a, which also makes it possible to selectively cause silver to diffuse.

Molten silver has low wettability with the ceramic layer, and therefore molten silver droplets tend to aggregate together. Therefore, silver (or a silver alloy) that has decreased in volume through diffusion does not spread in the form of thin film over the surface of the ceramic layer. Instead, lumps of aggregated silver (or a silver alloy) are scattered on the ceramic surface. Therefore, metallic lumps that have aggregated to certain sizes tend to be scattered on the ceramic layer (or between two ceramic layers). Thus the metal layer having a high void ratio can be formed.

It is preferable that the high-content metallic paste layer 11a contains platinum as well as silver, and the metallic paste layer 13a contains platinum as well as palladium. When fired, silver reacts selectively with palladium to form an alloy. Presence of platinum that has slower diffusion rate than palladium at the same temperature causes a part of silver to form an alloy with platinum. As a result, silver can be prevented from excessively diffusing even when fired in such a manner as a ship temperature gradient is generated in the stacked compact 17a or the temperature rises quickly.

Thus the metal layer can be prevented from completely disappearing due to the diffusion of entire silver and palladium contained in the metallic paste, since a part of silver forms an alloy with platinum. This makes it possible to greatly expand the permissible ranges of firing conditions that allow diffusion to occur and, at the same time, prevent the metal layer from disappearing. It is particularly preferable to mix platinum in both the metallic paste layer 11a and the metallic paste layer 13a.

A case in which the metal component $M_1$ is silver (Ag) and the metal component $M_2$ is palladium (Pd) will be taken in the detailed description that follows. The high-content metallic paste layer 11a has at least one of an alloy powder containing Ag in such forms as an Ag—Pd alloy or an Ag—Pt alloy and a metal powder made of Ag added thereto. The metallic paste layer 13a has at least one of an alloy powder containing Ag and Pd such as an Ag—Pd alloy and a mixed powder containing Ag powder and Pd powder added thereto.

A Pd powder has higher tendency to be oxidized at a low temperature than Pd contained in an Ag—Pd alloy. Thus use of the Pd powder may cause the metal layer to increase in volume due to oxidization during firing, in comparison to a case in which an Ag—Pd alloy is used in preparation of the metallic paste. Therefore, in case the metal component $M_2$ is palladium (Pd), it is preferable to use an Ag—Pd alloy when preparing the metallic paste. It is particularly preferable to use a mixed powder of an Ag powder and an Ag—Pd alloy powder, which achieves faster and stable diffusion because Ag that has a lower melting point begins to diffuse earlier so as to increase the Ag concentration in the Ag—Pd alloy and induces the diffusion.

The ceramic green sheet 15a that is not yet fired consists of a powder of the ceramic material of which particles are bound together by the binder. In a stage during sintering shown in FIG. 2(b), the binder is vaporized by heating to leave tiny voids between the ceramic particles. As the firing temperature rises further, the ceramic particles begin to sinter with each other and the metal powder contained in the metallic paste layer that has been printed also begins to sinter.

Then liquid phase is formed between the ceramic particles and between the metal particles, while the rate of diffusion among the particles increases so as to accelerate the sintering process. In this process, the presence of the tiny voids between the ceramic particles and the presence of the liquid phase between the ceramic particles and between the metal particles make mutual diffusion of the metallic components possible through the ceramic layer 15b between the porous metal layer 11b and the metal layer 13b in the course of sintering.

In this embodiment, the mass percentage X of the porous metal layer 11b is set to be higher than the mass percentage of the metal layer 13b. By making the metal layers to include the same metal with different mass percentages, it is supposed that silver contained in the porous metal layer 11b is caused to diffuse through the ceramic layer 15b into the metal layer 13b during the sintering process.

As the firing temperature rises further, voids between the ceramic particles diminish or disappear, so that diffusion of silver through the ceramic layer 15 comes to an end as shown in FIG. 2(c). As sintering of the ceramic particles completes, sintering of the porous metal layer 11 and the metal layer 13 also completes.

In the porous metal layer 11, silver or a silver-palladium alloy aggregates due to high fluidity in the state of liquid phase in the course of sintering, in addition to the decrease in volume due to the diffusion of silver into the metal layer 13. As a result, the porous metal layer 11 is formed in such a constitution as, rather than the metal component evenly covering the surface of the ceramic layer 15, porous structure with plural separate bubbles are included inside, or plural metal lumps are disposed therein via the voids as shown in FIG. 12 and described later.

The metal layer 13, on the other hand, has relatively high density since silver diffuses from the porous metal layer 11 thereto. It is preferable to add a sintering assisting agent to the ceramic green sheet 15a and the metallic paste, so as to make liquid phase easier to be formed during the sintering process.

The porous metal layer 11 and the metal layer 13 include the metal component M. It is preferable that mass percentage Y is higher in the porous metal layer 11 than in the metal layer 13 that adjoins therewith in the stacking direction, the mass percentage Y being the concentration of the metal component $M_1$ in proportion to the total metal content in the metal layer.

When the ceramic member is placed for use in an environment subjected to high temperature, migration may occur when there is a difference in composition between the metal layers. When the mass percentage Y in the porous metal layer 11 is higher than that in the metal layer 13, the metal component $M_1$ can be suppressed from moving from the metal layer 13 toward the porous metal layer 11. As a result, high void ratio in the porous metal layer 11 can be maintained. Thus sensor function and stress relieving function that are achieved by high void ratio are maintained so as to make the ceramic member having high durability.

Figure 3:
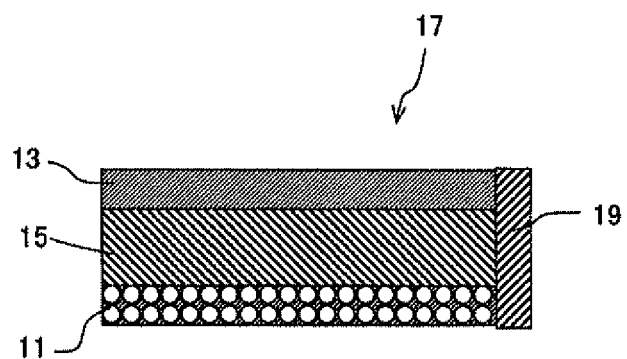
FIG. 3 is a sectional view showing one form of the ceramic member shown in FIG. 1 having external electrodes formed on side faces thereof.

FIG. 3 is a sectional view of the ceramic member having external electrodes 19 formed on the side faces thereof. The external electrodes may be formed, for example, as follows. A metallic paste is prepared by mixing a metal powder, a binder, a plasticizer and the like. The metallic paste is printed at a predetermined position, dried and fired. The metallic paste may be printed on the surface of the ceramic member as it is, although it is preferable to make the surface smooth by polishing or the like before printing the paste thereon. Other portions will be identified by the same reference numerals as those of FIG. 1, and description thereof will be omitted.

In this embodiment, the expression that "there are many voids" means that the voids occupy a large portion of the sectional area of the metal layer. A void ratio can be compared between the porous metal layer 11 and the metal layer 13 that adjoins therewith, as follows. A section of the porous metal layer 11 and a section of the metal layer 13 (a section parallel to the stacking direction, or a section perpendicular to the stacking direction) are observed under a scanning electron microscope (SEM), metallurgical microscope, optical microscope or the like to obtain images of the sections and the images are compared. When an apparent difference in the number of voids can be seen in the image of the section between the porous metal layer 11 and the metal layer 13, comparison may be made by observation with naked eyes. When difference in the number of voids cannot be recognized between the porous metal layer 11 and the metal layer 13, comparison may be made by measuring the void ratio with the method described below.

The void ratio in the metal layer of the ceramic member can be measured as follows. First, the ceramic member is polished along the stacking direction by a known polishing machine so as to reveal a section the metal layer or the metal layer (a section parallel to the stacking direction, or a section perpendicular to the stacking direction) in which the void ratio is to be measured. Polishing operation may be done, for example, by using a desktop polishing machine KEMET-V-300 manufactured by KEMET Japan Inc. and a diamond paste.

The void ratio may be measured by observing the section exposed by this polishing operation, under a scanning electron microscope (SEM), metallurgical microscope, optical microscope or the like and processing an image of the section taken in this observation. Power of magnification of the SEM or the like in this observation is preferably about 1,000 to 10,000.

When a section of the metal layer is to be observed, it is preferable to polish the metal layer to a depth of about one half of the thickness thereof, and observe the section exposed thereby. In case the metal layer is thin and has significantly varying thickness, it may be impossible to expose the entire section of the metal layer by polishing. In such a case, the metal layer may be polished until a part thereof is exposed with an image of that part taken, and may be polished further to expose other part to observe the newly exposed part, with this operation repeated several times. The images obtained by these repetitive polishing and observing operations may be combined so as to obtain the overall sectional view of the metal layer.

The image processing may be carried out as follows. For example, on an image of the section obtained by using an optical microscope, the portions representing the voids are painted in black and the rest is painted in white, then the void ratio can be calculated as (Area of black portions)/(Area of black portions+area of white portions) and given in terms of in percentage.

Figure 4:
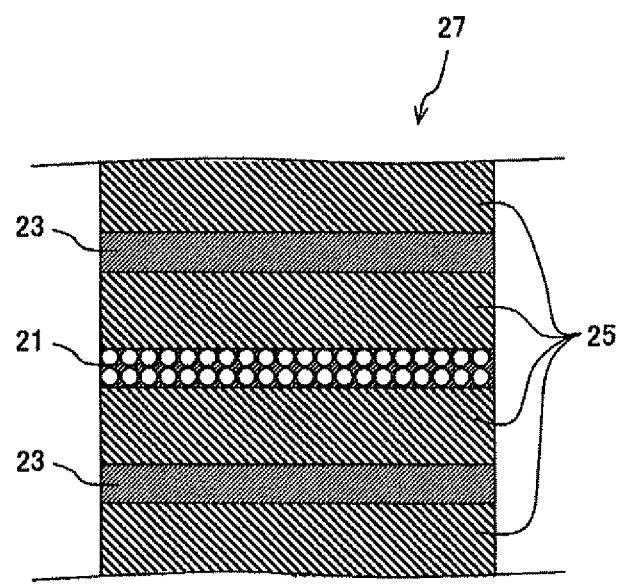
FIG. 4 is a sectional view showing a ceramic member according to another embodiment of the present invention.

The image data may also be input to a computer, so as to determine the void ratio by means of image processing software. In case the image of the section is a colored picture, the image may be converted to gray scale and divided into black portions and white portions. If it is required to set a threshold that separates two tones of black and white, the threshold may be set by means of the image processing software or by visual inspection FIG. 4 is a sectional view of a ceramic member 27 according to another embodiment of the present invention. As shown in FIG. 4, the ceramic member 27 is constituted from metal layers 21, 23 that are stacked one on another via a ceramic layer 25.

The metal layer 21 has a higher void ratio than the metal layers 22, 23 that adjoins therewith on both sides thereof in the stacking direction have. The metal layer 21 may be hereafter referred to as porous metal layer 21. The metal layers 21, 23 include the metal component $M_1$. Let the mass percentage of the metal component $M_1$ in proportion to the total metal content in the metal layer be Y. Then it is preferable that the metal layer 21 has higher mass percentage Y than the metal layers 22, 23 that adjoin therewith on both sides thereof in the stacking direction have.

The ceramic member 27 includes two three-layer structures where the metal layer 23 (the first metal layer 23) containing the metal component $M_1$ and the porous metal layer 21 (the second metal layer 21) that has more voids than the metal layer 23 sandwich the ceramic layer 25. The ceramic member 27 also has five-layer structure comprising two three-layer structures that share the porous metal layer 21 (the second metal layer 21).

A method according to the present invention for manufacturing the ceramic member 27 that has the porous metal layer 21 will be described below. FIG. 5(a) to FIG. 5(c) are schematic diagrams showing the method of manufacturing the ceramic member of this embodiment. This manufacturing method comprises the steps of forming a stacked compact 27a from a first metallic paste layer 23a and a second metallic paste layer 21a that are stacked one on another via the ceramic green sheet 25a, and firing the stacked compact 27a.

The ceramic green sheet and the metallic paste are prepared similarly as described previously. The first metallic paste layer 23a or the second metallic paste layer 21a is formed on one of the principal surfaces of plural ceramic green sheets 25a by a screen printing method or the like, and the ceramic green sheets are stacked one on another so that the first metallic paste layers 23a are disposed on both sides of the second metallic paste layer 21a in the stacking direction, thereby forming the stacked compact 27a (FIG. 5(a)).

The first metallic paste layer 23a and the second metallic paste layer 21a contain the metal component $M_1$ as the main component. The second metallic paste layer 21a is prepared to have a higher mass percentage X than that of the first metallic paste layers 23a, 23a that are disposed on both sides of the metallic paste layer 21a in the stacking direction. Hereafter the second metallic paste layer 21a will be called the high-content metallic paste layer 21a.

This embodiment is different from the basic structure described previously in that the metallic paste layers 23a are disposed on both sides of the high-content metallic paste layer 21a in the stacking direction. In case the metallic paste layers 23a are disposed on both sides of the metallic paste layer 21a, the metal component $M_1$ contained in the high-content metallic paste layer 21a is caused to diffuse into the metallic paste layers 23a that are disposed on both sides thereof by firing the stacked compact 27a.

The stacked compact 27a shown in FIG. 5(a) is turned into the ceramic member 27 shown in FIG. 5(c) through a stage during sintering shown in FIG. 5(b). The metal layers 23, 23 have relatively high density as the metal component diffuses from the porous metal layer 21 thereto.

Figure 6:
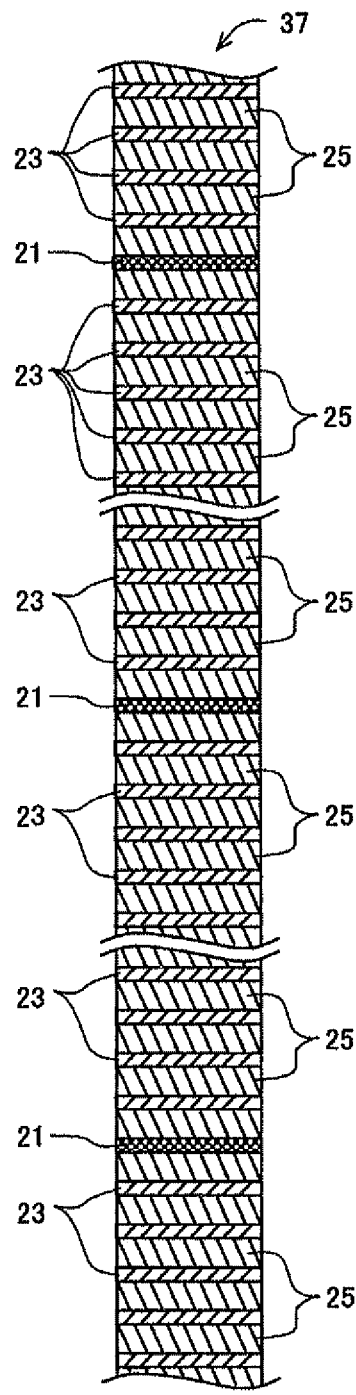
FIG. 6 is a sectional view showing a ceramic member according to further another embodiment of the present invention.

FIG. 6 is a sectional view showing a ceramic member according to further another embodiment of the present invention. As shown in FIG. 6, the ceramic member 37 is constituted by stacking the porous metal layer 21 and the metal layer 23 one on another via the ceramic layer 25. In this ceramic member 37, plural porous metal layers 21 are disposed in the stacking direction. These porous metal layers 21 are disposed with plural metal layers 23 interposed therebetween. The porous metal layers 21 are disposed regularly (at predetermined intervals) in the stacking direction. Specifically, a predetermined number of metal layers 23 are disposed between the porous metal layers 21.

A method for manufacturing a ceramic member 37 having the above-mentioned plural porous metal layers 21 according to the present invention will now be described. The ceramic green sheet 25a, the metallic paste layer 23a and the high-content metallic paste layer 21a are prepared similarly as described previously. The metallic paste layer 23a or the high-content metallic paste layer 21a is formed on the principal surface of the ceramic green sheets 25a by printing.

The ceramic green sheets 25a are stacked one on another so that the high-content metallic paste layers 21a sandwich plural metallic paste layers 23a, and the high-content metallic paste layers 21a are disposed regularly in the stacking direction, thereby forming the stacked compact. This stacked compact is fired to obtain the ceramic member 37.

Figure 7:
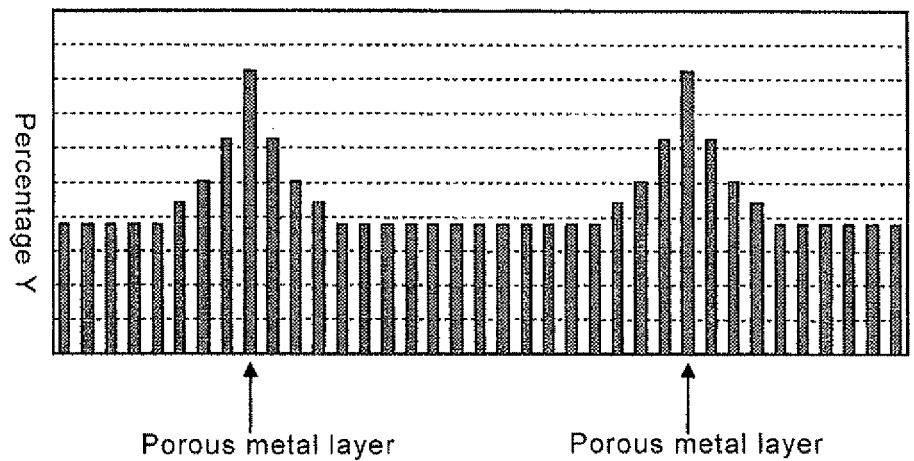
FIG. 7 is a graph schematically showing the characteristics of the embodiment shown in FIG. 6.

The ceramic member 37 having the characteristics shown in FIG. 7 is obtained by controlling the firing conditions and adjusting the amount of metal component $M_1$ that diffuses from the high-content metallic paste layer 21a into the metallic paste layer 23a. In the ceramic member 37 having the characteristics shown in FIG. 7, mass percentage Y peaks in the porous metal layer 21 and gradually decreases from the porous metal layer 21 over at least two metal layers 23 toward both ends in the stacking direction. The mass percentage Y shows the profile shown in FIG. 7, for the following reason.

The porous metal layer 21b is formed so as to have a mass percentage X higher than the mass percentage in the metal layer 23b, as mentioned previously. As the mass percentage of the same metal is differentiated among the metal layers, the metal component of the porous metal layer 21b diffuses to the metal layer 23b through the ceramic layer 25b depending on the mass percentage of the metal component. Since this metal layer 23b has higher mass percentage Y of the metal component $M_1$ than that of the metal layer 23b that adjoins this metal layer 23b, gradient of concentration is generated also between these metal layers 23b, 23b.

As a result, the gradient of concentration drives the metal component to diffuse from the metal layer 23b to the other metal layer 23b. This diffusion movement proceeds from the porous metal layer 21b over two or more metal layers 23b toward both ends in the stacking direction. Thus the ceramic member 37 having such a structure as the mass percentage Y peaks in the porous metal layer 21 and gradually decreases from the porous metal layer 21 over at least two metal layers 23 toward both ends in the stacking direction can be obtained.

As the firing time is elongated, the difference in mass percentage Y among the metal layers decreases, eventually becoming zero.

The ceramic member 37 having such a structure has an advantage of high strength to endure thermal shock since concentration of the metal component decreases gradually without abrupt change. This is due to the fact that the metal has higher heat conductivity than the ceramics, and that heat conductivity changes with the composition of the metal component. That is, as the concentration of the metal component decreases gradually without abrupt change heat conductivity in the ceramic member can be suppressed from changing.

Figure 8:
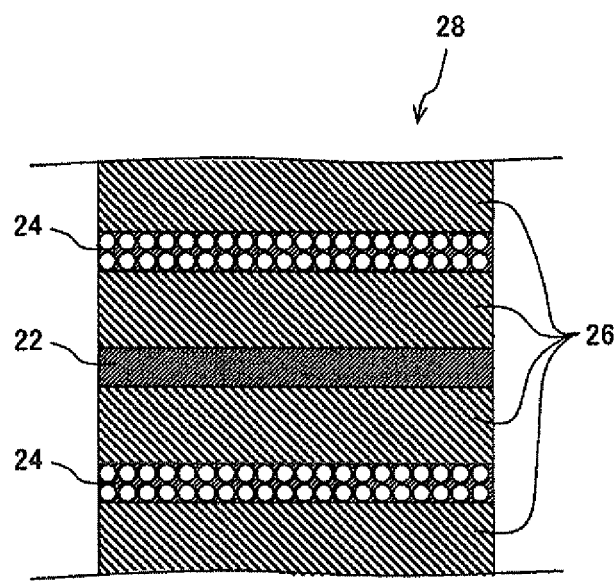
FIG. 8 is a sectional view showing a ceramic member according to further another embodiment of the present invention.

FIG. 8 is a sectional view showing a ceramic member according to further another embodiment of the present invention. As shown in FIG. 8, the ceramic member 28 is constituted by stacking metal layers 22, 24 one on another via a ceramic layer 26. The metal layers 22, 24 contain the metal component $M_1$. The metal layers 24 that are disposed on both sides of the metal layer 22 are prepared to have a lower mass percentage Y and a higher void ratio than those of the metal layer 22. Hereafter the metal layer 24 will be called the porous metal layer 24.

The ceramic member 28 includes two three-layer structures where the metal layer 22 (the first metal layer 22) containing the metal component $M_1$ and the porous metal layer 24 (the second metal layer 24) that has more voids than the metal layer 22 sandwich the ceramic layer 26. The ceramic member 28 also has a five-layer structure comprising two three-layer structures that share the metal layer 22 (the first metal layer 22).

Figure 9A:
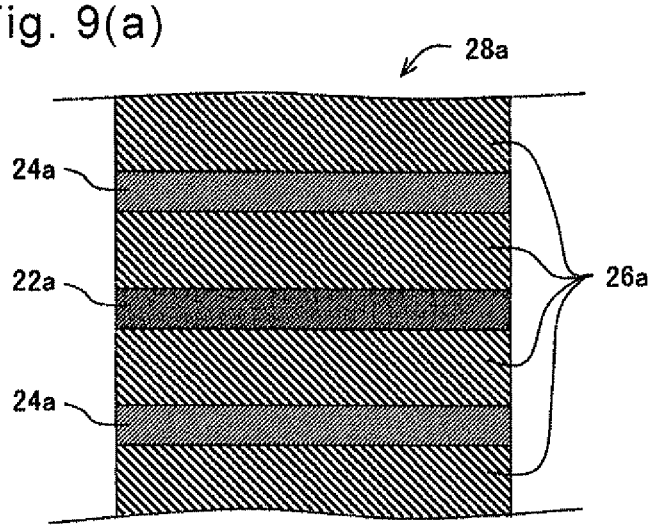
FIG. 9(a) to FIG. 9(c) are schematic diagrams showing the method of manufacturing the ceramic member according to the embodiment shown in FIG. 8.
Figure 9B:
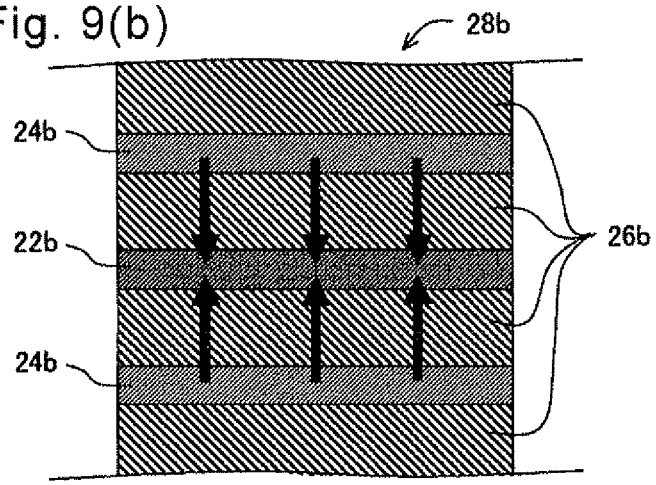
Figure 9C:
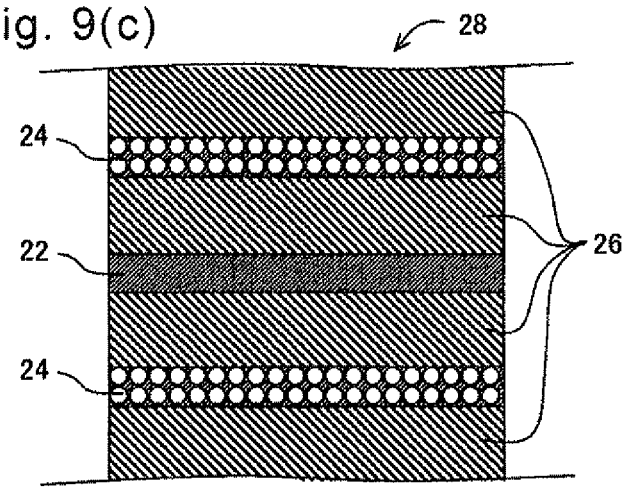

A method for manufacturing a ceramic member 28 having the porous metal layer 24 according to the present invention will now be described. FIG. 9(a) to FIG. 9(c) are schematic diagrams showing the method for manufacturing a ceramic member according to the embodiment shown in FIG. 8. This manufacturing method comprises the steps of forming a stacked compact 28a from metallic paste layers 22a, 24a that are stacked one on another via ceramic green sheet 26a, and firing the stacked compact 28a.

The ceramic green sheet and the metallic paste are prepared similarly as described previously. First, plural ceramic green sheets 26a are formed, and the metallic paste layer 22a or 24a is formed on one principal surface of each ceramic green sheet 26a by a screen printing method or the like, and the ceramic green sheets are stacked one on another so that the metallic paste layers 24a are disposed on both sides of the metallic paste layer 22a in the stacking direction, thereby forming the stacked compact 28a (FIG. 9(a)).

The metallic paste layer 22a and the metallic paste layer 24a contain the metal component $M_1$ as the main component. The metallic paste layer 22a is prepared to have a lower mass percentage X than that of the metallic paste layers 24a, 24a disposed on both sides of the metallic paste layer 22a in the stacking direction. Hereafter the metallic paste layer 22a will be called the low-content metallic paste layer 22a.

This embodiment is different from the basic structure described previously in that the metallic paste layers 24a are disposed on both sides of the low-content metallic paste layer 22a. In case the metallic paste layers 24a are disposed on both sides of the metallic paste layer 22a, the metal component $M_1$ contained in the metallic paste layers 24a that are disposed on both sides diffuses into the low-content metallic paste layer 22a when the stacked compact 28a is fired.

In this embodiment, the metal layer 22b sandwiched by the porous metal layers 24b is formed so as to have mass percentage X that is lower than the mass percentage in the metal layers 24b, 24b. As the mass percentage of the same metal is differentiated among the metal layers, the metal component of the porous metal layers 24b disposed on both sides diffuses through the ceramic layer 26b that is in the course of sintering from both sides of the metal layer 22b depending on the mass percentage of the metal component (FIG. 9(b)). Thus the ceramic member 28 as shown in FIG. 9(c) is obtained (FIG. 9(c)). The metal layers 22 have relatively high density as the metal component diffuses from the porous metal layer 24 thereto.

The mass percentage X in the low-content metallic paste layer 22a may be set lower than that in the metallic paste layers 24a that adjoin therewith on both sides thereof in the stacking direction. There is no restriction on the difference in mass percentage between these layers (mass percentage XH in the metallic paste layer 24a minus mass percentage XL in the low-content metallic paste layer 22a).

In a case the metal component $M_1$ is silver, and the metal component $M_2$ is palladium or platinum, the difference in mass percentage X is preferably in a range described below. In order to promote diffusion of the metal component $M_1$, the difference in mass percentage is preferably 0.1 or larger. On the other hand, the difference in mass percentage is preferably not larger than 30, in order to suppress the metal component $M_1$ from excessively diffusing into the metallic paste layer 22a and causing adjacent ceramic layers to join with each other. Thus the difference in mass percentage is preferably in a range from 0.1 to 30.

In order to increase the diffusion rate of the metal component $M_1$, the difference in mass percentage is preferably 1 or larger as described above. For the purpose of causing the mutual diffusion described above more vigorously, the difference in mass percentage is preferably 2 or larger.

In the case of this embodiment, silver diffuses from the metallic paste layers 24a that are disposed on both sides of the low-content metallic paste layer 22a in the stacking direction into the low-content metallic paste layer 22a. In the case of this form, the difference in mass percentage is more preferably 25 or less in order to suppress the diffusion rate of the metal component $M_1$ and increase the density of the ceramics after sintering.

Since the temperature at which sintering begins varies depending on the difference in mass percentage X, difference in mass percentage is preferably 10 or larger in order to stabilize the timing at which diffusion of the metal component $M_1$ from the two metallic paste layers 24a into the low-content metallic paste layer 22a begins, even when the temperature distribution of the ceramic member becomes uneven while the temperature is being raised in the furnace. Accordingly, the difference in mass percentage is preferably in a range from 10 to 25.

Figure 10:
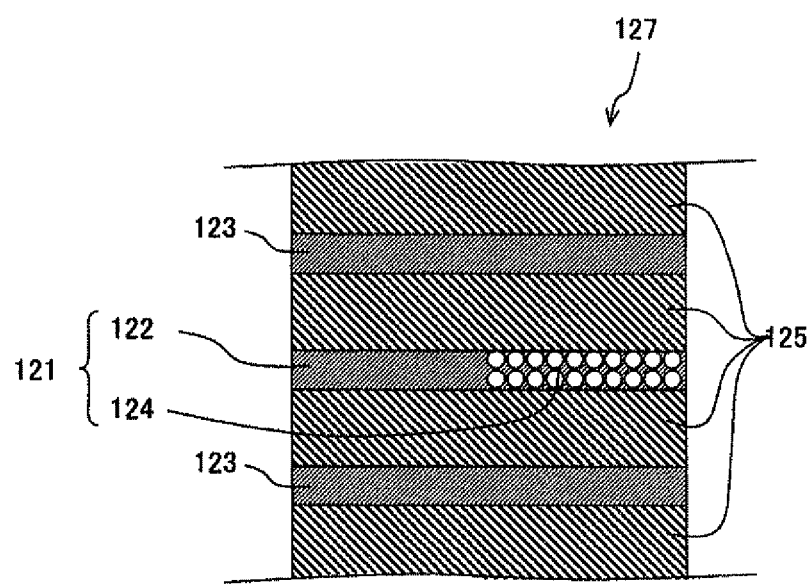
FIG. 10 is a sectional view showing a ceramic member according to further another embodiment of the present invention.

FIG. 10 is a sectional view showing a ceramic member 127 according to further another embodiment of the present invention. As shown in FIG. 10, the ceramic member 127 is constituted by stacking metal layer 121, 123 one on another via a ceramic layer 125.

The metal layers 121, 123 contain the metal component $M_1$. The metal layer 121 has an area 124 formed in a part of the metal layer 121 where more voids are included than in other area 122. It is preferable that the area 124 has a higher mass percentage Y and higher void ratio than those in the other area 124 and in the metal layer 123. Hereafter the area 124 will be referred to as porous area 124.

Figure 11A:
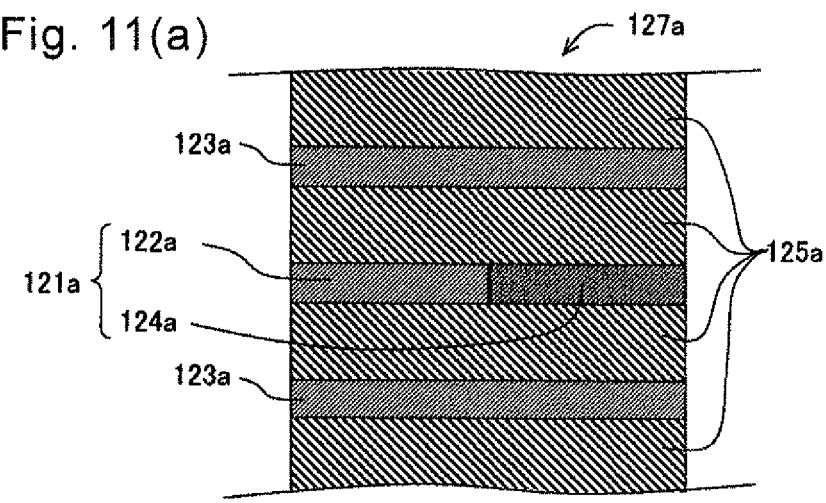
FIG. 11(a) to FIG. 11(c) are schematic diagrams showing the method of manufacturing the ceramic member according to the embodiment shown in FIG. 10.
Figure 11B:
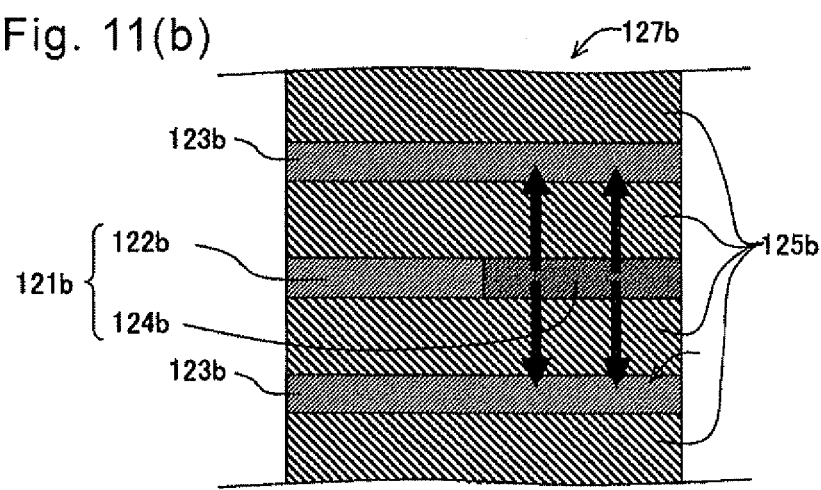
Figure 11C:
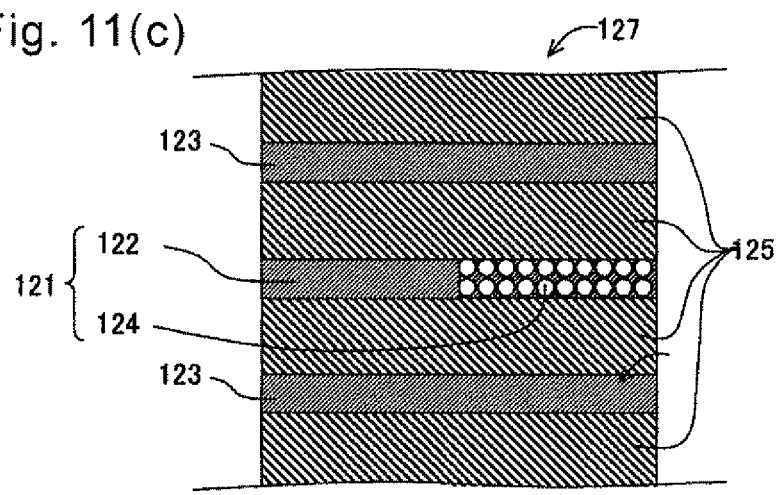

A method for manufacturing a ceramic member 127 that has the porous area 124 in the metal layer 121 according to the present invention will now be described. FIG. 11(a) to FIG. 11(c) are schematic diagrams showing the method of manufacturing the ceramic member according to this embodiment.

This manufacturing method comprises the steps of forming a stacked compact 127a from metallic paste layers 121a, 123a that are stacked one on another via a ceramic green sheet 125a, and firing the stacked compact 127a.

The ceramic green sheet and the metallic paste are prepared similarly as described previously. First, plural ceramic green sheets 125a are formed, and the metallic paste layer 121a or 123a is formed on one principal surface of each ceramic green sheet 125a by a screen printing method or the like, and the ceramic green sheets are stacked one on another so that the metallic paste layers 123a are disposed on both sides of the metallic paste layer 121a in the stacking direction, thereby forming the stacked compact 127a (FIG. 11(a)). The metallic paste layer 121a comprises the metallic paste layer 122a for the other layer 122 and the metallic paste layer 124a for a part of the metal layer 124.

The metallic paste layer 121a (122a, 124a) and the metallic paste layer 123a include the metal component $M_1$ as the main component. The metallic paste layer 124a is prepared to have higher mass percentage X than that of the metallic paste layer 122a and higher mass percentage X than that of the metallic paste layers 123a, 123a that adjoin therewith on both sides thereof in the stacking direction. Hereafter the metallic paste layer 124a will be called the high-content metallic paste layer 121a.

In case the metallic paste layers 123a are disposed on both sides of the high-content metallic paste layer 124a, the metal component $M_1$ contained in the high-content metallic paste layer 124a is caused to diffuse preferentially into the metallic paste layers 123a disposed on both sides thereof, rather than diffuse within the plane, when the stacked compact 127a is fired.

The stacked compact 127a shown in FIG. 11(a) is turned into the ceramic member 127 shown in FIG. 11(c) through a stage during sintering shown in FIG. 11(b). The areas (porous area 124 and the other area 122) that have different void ratios can be formed within the same layer in this way.

FIG. 12 is a sectional view showing a ceramic member according to further another embodiment of the present invention. As shown in FIG. 12, the ceramic member 27' comprises the porous metal layer 29 that is constituted from plural metal lumps (or partial metal layers) 29a, 29a, . . . dispersed between the ceramic layers 25, 25 that adjoin the porous metal layer 29 in the stacking direction, and these metal lumps 29a are disposed separately from each other.

Plural metal lumps 29a are electrically isolated from each other by the voids 29b. That is, the porous metal layer 29 includes plural metal lumps 29a dispersed on the ceramic layer 25 in plan view of the porous metal layer 29. Since the metal lumps 29a are disposed while being separated from each other by the voids, the porous metal layer 29 functions as a good stress relieving layer and also as a good insulator.

The ceramic member as described above can be used as a gas sensor by forming the ceramic layer from a ceramic material such as $ZnO$, $SnO_2$, $TiO_2$ or $ZrO_2$ that is commonly used in gas sensors and measuring the electrical resistance of the ceramic layer while flowing electrical current through the metal layer and the porous metal layer. By using a ceramic material that functions as a solid electrolyte such as $ZrO_2$ to form the ceramic layer, a fuel cell can be made that generates electromotive force from the metal layer and the porous metal layer when exposed to a predetermined atmosphere. When the ceramic layer is formed from a piezoelectric material such as $BaTiO_3$, lead titanate zirconate (PZT) or ZnO, a piezoelectric device can be made that is driven by flowing electrical current through the metal layer and the porous metal layer or generates electromotive force.

There is no restriction on the void ratio of the porous metal layer of the ceramic member of the present invention, which may be determined in accordance to the application. The void ratio may be varied by controlling the mass percentage X, firing time, firing temperature and/or other factors.

Gas Sensor Device

The ceramic member 17 shown in FIG. 1 can be used as a gas sensor device. When the ceramic member 17 is applied to a gas sensor device, the ceramic layer 15 may be formed from a ceramic material that shows the property of oxide semiconductor such as $ZnO$, $SnO_2$ or $TiO_2$. The device formed from the ceramic material of oxide semiconductor as described above functions as a gas sensor by measuring the electrical resistance of the ceramic layer 15 while flowing electrical current through the metal layer 13 and the porous metal layer 11.

The ceramic layer 15 may also be formed a solid electrolyte such as $ZrO_2$. When two gases having different oxygen concentrations are separated from each other by the ceramic layer 15, motions of oxygen ions and free electrons are caused in the ceramic layer 15 due to the difference in the oxygen concentration.

When used in an atmosphere of high temperature, there has been such a problem in the prior art as the electrode component moves by diffusion. According to the present invention, since the metal layer 13 and the metal layer 11 having a high void ratio contain the metal component $M_1$ as the main component, difference in the ionization tendency and difference in the electronegativity can be suppressed to low levels. As a result, a device of high durability that can be used stably can be made since movement of the metal ions and diffusion of metal can be minimized when the device is used as a cell.

An oxygen sensor can be made by disposing the ceramic layer 15 always in contact with the atmosphere and bringing a gas to be measured into contact with the other side opposite to the ceramic layer 15. At this time, the gas to be detected may be put into contact with the porous metal layer 11 that has a higher void ratio, and the atmosphere may be put into contact with the metal layer 13 as a reference gas.

Figure 13:
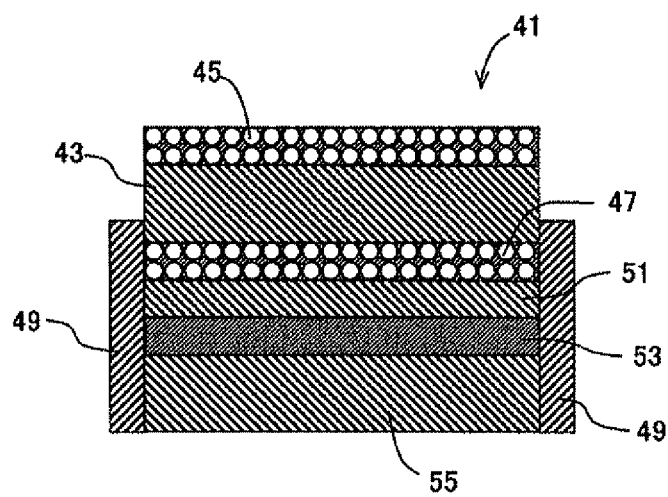
FIG. 13 is a sectional view showing a gas sensor device according to one embodiment of the present invention.

FIG. 13 is a sectional view of a gas sensor device having good characteristics according to another embodiment of the present invention. The gas sensor device 41 uses a solid electrolyte represented by $ZrO_2$ in the ceramic layer 43. The gas to be detected is put into contact with the metal layer 45 that has a high void ratio and the atmospheric air is put into contact with the porous metal layer 47 that has a high void ratio. The porous metal layer 47 is sealed on the circumference thereof by external electrode 49 and a ceramics layer 51, to prevent the gas that is in contact with the metal layer 45 from making contact with the porous metal layer 47. This makes it possible for gases having difference oxygen concentrations to make contact with the principal surfaces on both sides of the ceramic layer 43 made of the solid electrolyte material.

Detected signal can be transmitted at a high speed through dense electrode (metal layer 53) by connecting the relatively dense metal layer 53 to the external electrode 49. This means that the external electrode 49 functions as a guide for introducing the atmospheric air as the reference gas, and also functions as the medium for high speed transmission of the signal.

When the metal layer 53 is embedded between the ceramic layer 51 and the ceramic layer 55, a device of high durability can be made since oxidation of the metal layer 53 can be suppressed even when the gas sensor device is exposed to an atmosphere of high temperature.

In case the ceramic layers 51, 55 are formed from alumina ceramics that has high heat resistance and high heat conductivity, such an oxygen sensor can be made that is capable of quick heating and quick startup when the gas sensor device is heated.

When the ceramic layers 43, 51, 55 are formed from a solid electrolyte represented by $ZrO_2$, the amounts of shrinkage of the ceramic layers during firing can be made almost the same. As a result, it is made easier to fire and possible to decrease the stress generated by the difference in thermal expansion during firing. This makes the device highly durable.

Figure 14:
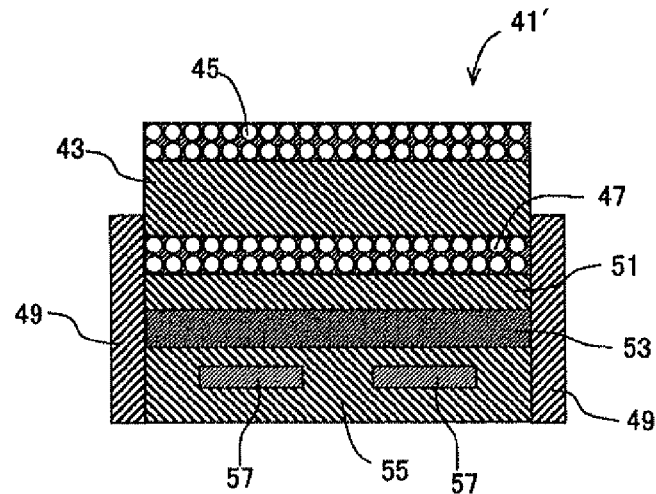
FIG. 14 is a sectional view showing a gas sensor device according to another embodiment of the present invention.

FIG. 14 is a sectional view of another embodiment of the gas sensor device. Such a heater-integrated oxygen sensor can be made that has a heater 57 incorporated in the ceramic layer 55.

A method for manufacturing a sensor device shown in FIG. 13 will be described. First, a $ZrO_2$ ceramic (stabilized zirconia) powder containing Ca and Y added thereto, the binder described above and the plasticizer described above are mixed to prepare a slurry. The slurry is then formed into a ceramic green sheet as described previously.

Then a metallic paste to be used to form the metal layer 53 is prepared. The metallic paste is prepared by mixing a metal powder consisting mainly of silver palladium, a binder and a plasticizer. The metallic paste is printed on one side of the ceramic green sheet by screen printing or the like.

Then a metallic paste (high-content metallic paste) to be used to form the porous metal layer 47 having a high void ratio is prepared. The metallic paste is prepared by mixing a metal powder consisting mainly of silver, a binder and a plasticizer. The metallic paste is printed on the ceramic green sheet by screen printing or the like.

A stacked compact is formed by stacking the ceramic green sheets having the metallic paste layers formed thereon and placing another green sheet on the high-content metallic paste layer, then drying the stack. The thickness of the metallic paste layer is preferably from about 1 to 40 m.

After heating the stacked compact to a predetermined temperature to remove the binder, the stacked compact is fired at a temperature from 800 to 1,000° C. This causes silver to diffuse from the metal layer 47 that has high silver concentration to the metal layer 53, thus resulting in the metal layer 47 having a high void ratio and the metal layer 53 having relatively higher density.

Then a metallic paste is prepared by mixing a metal powder consisting mainly of platinum, a binder and a plasticizer. The metallic paste is printed on the sintered stack at a position where the metal layer 45 is to be formed by screen printing or the like. As the stack is fired at a temperature from 800 to 1,000° C., the ceramic layer is sintered with high density, although platinum that has liquid phase point higher than that of the ceramic layer is not turned into a sintered material of high density, instead making the metal layer 45 of high void ratio. Even a higher void ratio may be obtained by using a metallic paste prepared by mixing a platinum powder having a mean particle size of about 1 μm and acrylic beads having a mean particle size of about 5 μm in proportion of about 50:50, which produces a more porous electrode.

After machining the sintered stack into desired dimensions, the external electrodes 49 are formed thereon. The external electrodes 49 are formed by preparing a metallic paste by mixing a metal powder consisting mainly of silver, a binder, a plasticizer and glass powder, and printing the metallic paste on the side faces of the sintered stack by screen printing or the like, then firing the stack at a temperature from 600 to 800° C.

The manufacturing process may be other than that described above and follow a known method of the prior art, except for the step in which silver diffuses from the metallic paste layer that has high silver concentration to the metallic paste layer that has low silver concentration, thus resulting in the metal layer 47 having a high void ratio and the metal layer 53 having relatively higher density.

The gas sensor device shown in FIG. 14 may be manufactured by adding such a step to the process described above, as a metallic paste prepared by mixing a metal powder consisting mainly of platinum, a binder, a plasticizer and glass powder is printed in the form of a heater in the ceramic green sheet that form the ceramic layer 55.

Figure 15:
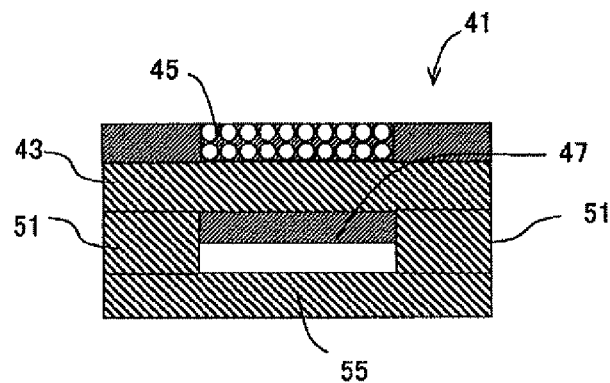
FIG. 15 is a sectional view showing a gas sensor device according to further another embodiment of the present invention.
Figure 16:
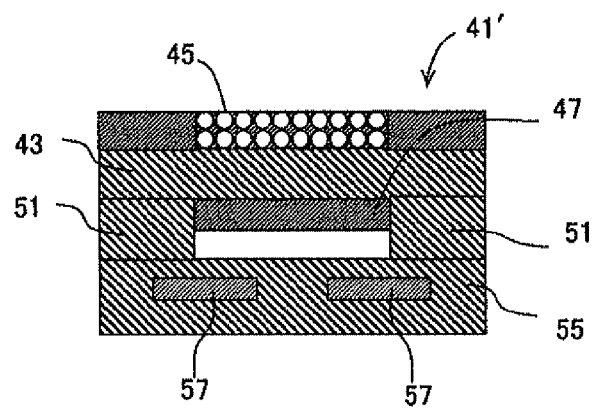
FIG. 16 is a sectional view showing a gas sensor device according to further another embodiment of the present invention.

FIG. 15 and FIG. 16 are sectional views of gas sensor devices according to other embodiments of the present invention.

The void ratio of the porous metal layer (the metal layer having a high void ratio) is preferably in a range from 30 to 90%, in order to ensure stable supply of gas and satisfactory durability of the metal layer. In order to mitigate the stress generated by the difference in thermal expansion between the electrode and the ceramics by utilizing the cushion effect of air, void ratio is more preferably in a range from 50 to 90%. Furthermore, in order to form a turbulent flow of supplied gas for stirring and form a laminar flow in the interface between the metal and the ceramics in the voids so as to improve the performance of gas detection, void ratio is more preferably in a range from 70 to 90% where a space that contains both a portion of turbulence and a portion of laminar flow is generated.

The void ratio of the metal layers other than the porous metal layer is preferably in a range from 0.1 to 40%, because higher density leads to higher electric conductivity that enables high speed transmission of signals. Since a metal has higher heat conductivity than ceramics has, a metal layer having higher density transmits heat to the ceramics at the start of sensor operation, thus making the sensor quicker in startup. With this regard, the void ratio is more preferably in a range from 0.1 to 20%.

Fuel Cell Device

Figure 17:
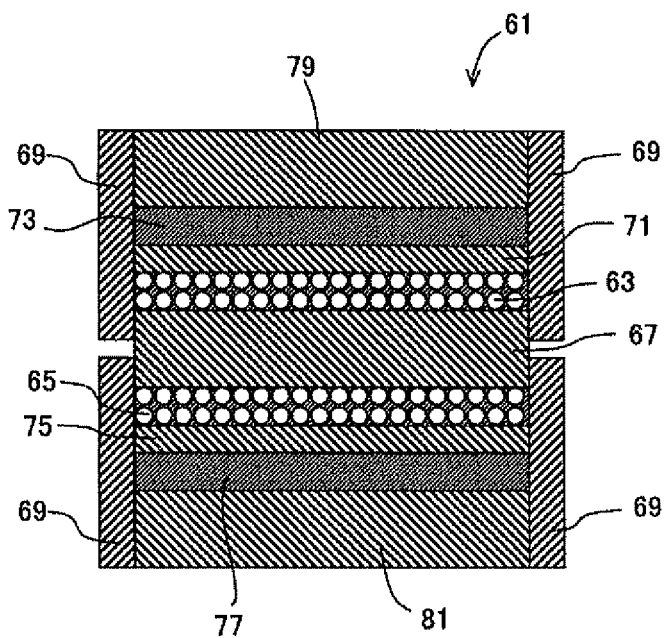
FIG. 17 is a sectional view showing a fuel cell device according to one embodiment of the present invention.

FIG. 17 is a sectional view of a fuel cell device according to one embodiment of the present invention. The fuel cell device can be made by utilizing the electromotive force generated by bringing gases having different oxygen concentrations into contact with a solid electrolyte, as described previously. To produce a large current, it is important to efficiently collect the electromotive force by packing many fuel cell devices in a limited volume.

As shown in FIG. 17, the fuel cell device 61 employs an electrode layer 63 that has a high void ratio for the layer through which oxygen flows (the so-called air electrode), and an electrode layer 65 that has a high void ratio is used also for the layer where oxygen concentration is very low (the so-called fuel electrode). A solid electrolyte represented by $ZrO_2$ is embedded in the ceramic layer 67 disposed between the electrode layers. This constitutes a basic portion of the fuel cell.

As the electrode layer 63 that serves as the air electrode can be sealed on the circumference thereof by the external electrode 69 and the ceramics layers 67, 71, a large quantity of oxygen can be caused to flow through the electrode layer 63 that has a high void ratio. Also because the electrode layer 73 that has high density is connected via the external electrode 69 to the electrode layer 63 that has a high void ratio, electromotive force can be efficiently transmitted.

As the electrode layer 65 that serves as the fuel electrode can be sealed on the circumference thereof by the external electrode 69 and the ceramics layers 67, 75, a large quantity of gas (for example, natural gas) having extremely low oxygen concentration can be caused to flow through the electrode layer 65 that has a high void ratio. Also because the electrode 77 that has high density is connected via the external electrode 69 to the electrode layer 65 that has a high void ratio, an electromotive force can be efficiently transmitted.

Efficiency of power generation by a fuel cell is improved when the cell is heated. In this regard, there has been such a problem that the electrode component moves through diffusion during operation at a high temperature. In contrast, the metal layers 73, 77 and the metal layers 63, 65 that have high void ratio include the metal component $M_1$ as the main component, and therefore can suppress the difference in the ionization tendency and difference in the electronegativity to low levels.

Figure 18:
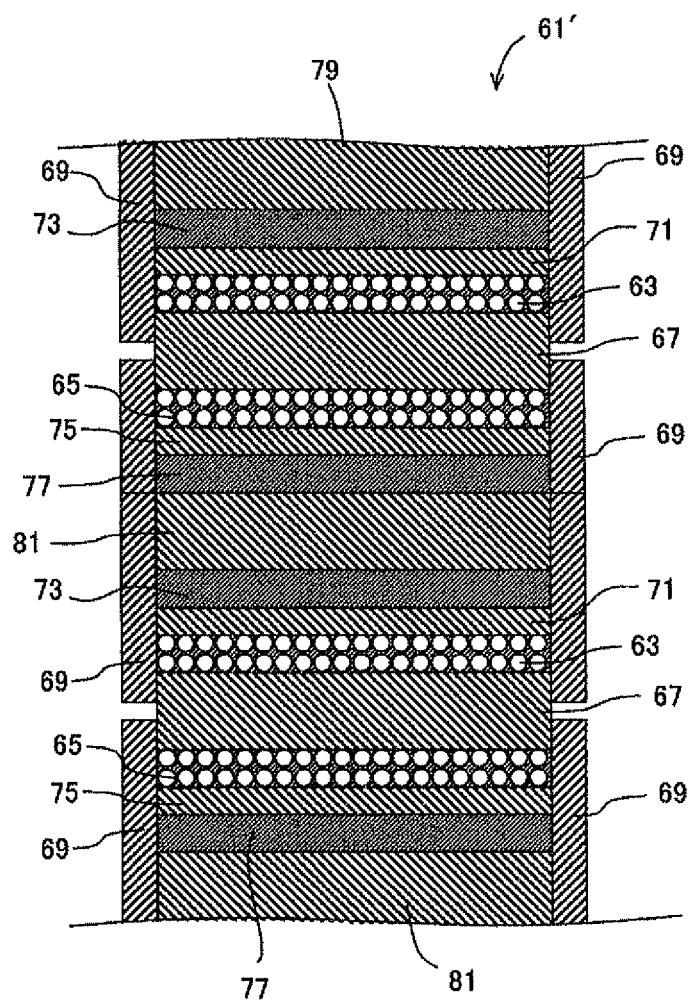
FIG. 18 is a sectional view showing a fuel cell device according to another embodiment of the present invention.

As a result, a device of high durability that can be used stably can be made since movement of the metal ions and diffusion of metal can be suppressed when the device is used as a cell. Moreover, a compact and high-density fuel cell device can be made by stacking the fuel cell devices and connecting the external electrodes of the same polarity together as shown in FIG. 18.

A method for manufacturing a fuel cell device shown in FIG. 17 will be described. First, a $ZrO_2$ ceramic (stabilized zirconia) powder containing Ca and Y added thereto, the binder described above and the plasticizer described above are mixed to prepare a slurry. Then ceramic green sheets for the ceramic layers 67, 71, 75, 79, 81 are made as described previously.

Then a metallic paste to be used to form the metal layers 73, 77 is prepared. The metallic paste is prepared by mixing a metal powder consisting mainly of silver palladium, a binder, a plasticizer, etc. The metallic paste is printed on one side of the ceramic green sheet by screen printing or the like.

Then a metallic paste used to form the metal layers 63, 65 having a high void ratio is prepared. The metallic paste is prepared by mixing a metal powder consisting mainly of silver, a binder, a plasticizer, etc. The metallic paste is printed on one side of the ceramic green sheet by screen printing or the like.

The green sheets having the metallic pastes printed thereon are stacked in such a structure as shown in FIG. 17 and dried, to make the stacked compact. The thickness of the metallic paste layer may be in a range from 1 to 40 µm in the case of screen printing.

After heating the stacked compact to a predetermined temperature to remove the binder, the stacked compact is fired at a temperature from 800 to 1,000° C. This causes silver to diffuse from the metal layer having a high silver concentration to the alloy layer, thus resulting in the metal layers 63, 65 having a high void ratio and the metal layers 73, 77 having relatively higher density.

After machining the sintered stack into desired dimensions, the external electrodes 69 are formed thereon. The external electrodes 69 are formed from a metallic paste prepared by mixing a metal powder consisting mainly of silver, a binder, a plasticizer, glass powder, etc., that is printed on the side faces of the sintered stack by screen printing or the like and is fired at a temperature from 600 to 800° C.

The manufacturing process may be other than that described above and follow a known method of the prior art, except for the step in which silver diffuses from the metallic paste layer that has high silver concentration into the metallic paste layer that has a low silver concentration, thus resulting in the metal layer 47 having a high void ratio and the metal layer 53 having relatively higher density. In the case of the form shown in FIG. 18, a necessary step among the steps described above may be added.

The void ratio of the porous metal layer is preferably in a range from 30 to 90%, in order to ensure stable supply of gas and durability of the metal layer. In order to mitigate the stress generated by the difference in the mal expansion between the electrode and the ceramics layers by utilizing the cushion effect of air, the void ratio is more preferably in a range from 50 to 90%.

Furthermore, in order to form a turbulent flow of supplied gas for stirring and form a laminar flow in the interface between the metal and the ceramics within the voids so as to improve the accuracy of the solid electrolyte to measure oxygen concentration, void ratio is more preferably in a range from 70 to 90%, where such a space can be produced that combines a portion of turbulent flow and a portion of laminar flow.

The void ratio of the metal layers other than the porous metal layer is preferably in a range from 0.1 to 40%, because higher density leads to higher electric conductivity that enables high speed transmission of signals. Since a metal has higher heat conductivity than ceramics, a metal layer having higher density transmits heat to the ceramics at the start of operation of the fuel cell, thus making the fuel cell device quicker in startup. With this regard, void ratio is more preferably in a range from 0.1 to 20%.

Multi-Layer Piezoelectric Device

Figure 19:
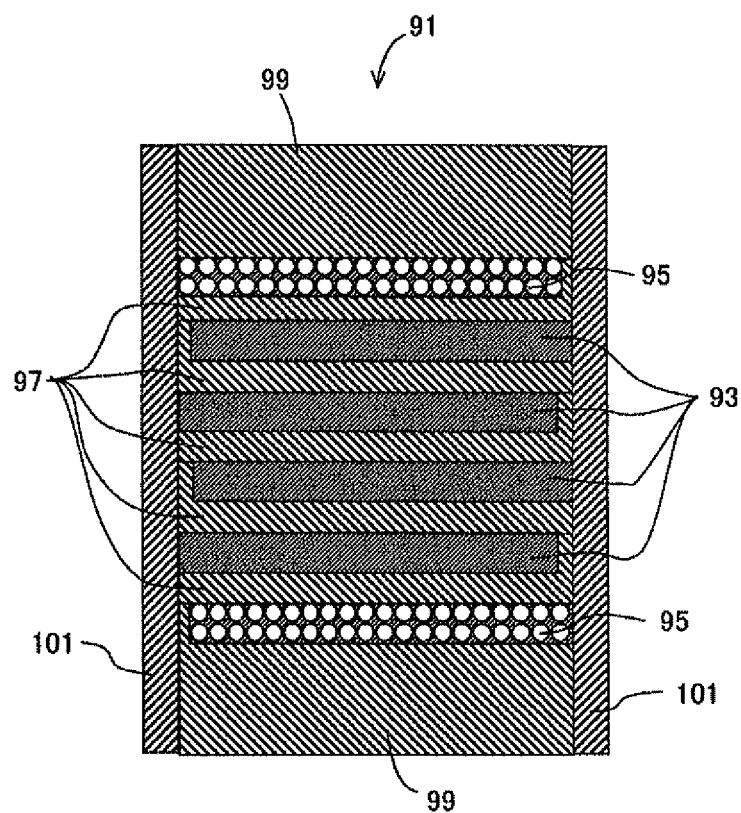
FIG. 19 is a sectional view showing a multi-layer piezoelectric device according to one embodiment of the present invention.

FIG. 19 is a sectional view of a multi-layer piezoelectric device according to one embodiment of the present invention. The multi-layer piezoelectric device 91 is constituted from a stack of plural first metal layers 93 that function as internal electrodes and second metal layers 95 which are stacked via the ceramic layer 97, with a pair of external electrodes 101, 101 formed on the side faces of the stack. The ceramic layers (inactive layers) 99 that do not contribute to the piezoelectric effect may be disposed on both ends of the stack in the stacking direction.

The second metal layer 95 has more voids than the first metal layer 93 that adjoins therewith in the stacking direction. The second metal layer 95 may be either a porous metal layer or formed from plural metal lumps that are separated from each other by the voids. Hereafter, the second metal layer 95 having any of these forms will be called the porous metal layer 11.

The ceramic layer 97 is formed from a piezoelectric material such as AZT (lead titanate zirconate). The metal layer 93 and the porous metal layer 95 are disposed such as to be exposed alternately on the opposing side faces of the stack. This constitution allows it to apply a voltage via the external electrodes 101 to the ceramic layers 97 that are disposed between the metal layers 93. Application of the voltage causes the device to contract and expand so as to function as a piezoelectric actuator.

In the multi-layer piezoelectric device 91, the porous metal layer 95 has a high void ratio and the metal layer 93 has relatively high density, and therefore voltage concentrates in the metal layer 93 that is dense and has high signal transmission speed. The porous metal layer 95 that has a high void ratio and high resistance receives relatively low voltage.

Since the porous metal layer 95 has a high void ratio, the area of the electrode through which the porous metal layer 95 contacts the adjacent ceramic layer 97 becomes smaller, and therefore the area of the ceramic layer 97 that deforms due to the reverse piezoelectric effect when a voltage is applied thereto becomes smaller than the ceramic layer 97 that adjoins the dense metal layer 93. As a result, the amount of piezoelectric displacement of the ceramic layer 97 sandwiched by the metal layers 93 becomes larger, and the amount of piezoelectric displacement of the ceramic layer 97 sandwiched by the metal layers of which at least one is the porous metal layer 95 having high voids ratio becomes smaller.

In this embodiment, the porous metal layer 95 having high a void ratio as described above is disposed to adjoin the ceramic layer 99 that is the inactive layer disposed in the border between a portion that is displaced and a portion that is not displaced, and therefore the porous metal layer 95 functions as a stress relieving layer. Since at least one of the internal electrodes that sandwich the ceramic layer 97 is the porous metal layer 95 that has a high void ratio and high resistance, the amount of piezoelectric displacement of the ceramic layer 97 that adjoins therewith becomes smaller, thus achieving the stress relieving effect. As a result, the multi-layer piezoelectric device having high durability can be made.

Figure 20:
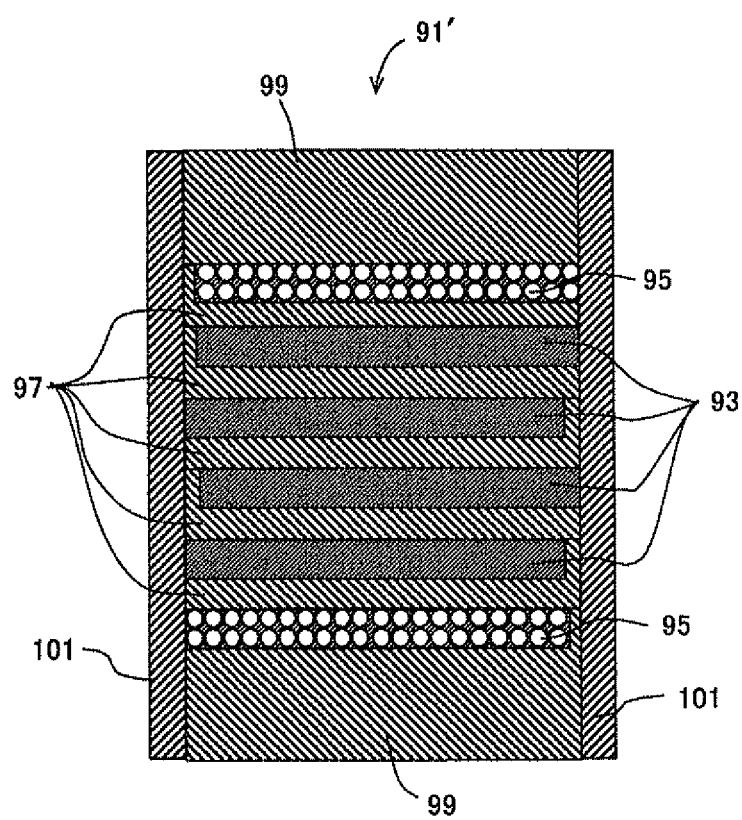
FIG. 20 is a sectional view showing a multi-layer piezoelectric device according to another embodiment of the present invention.

FIG. 20 is a sectional view of a multi-layer piezoelectric device 91' according to another embodiment of the present invention. The multi-layer piezoelectric device 91' is different from the multi-layer piezoelectric device 91 in that the porous metal layer 95 having a high void ratio is connected to the external electrode 101 of the same polarity as the metal layer 93 that adjoins the porous metal layer 95 that has a high void ratio. With this constitution, since voltage is not applied to the porous metal layer 95 and to the ceramic layer 97 that is sandwiched by the metal layers 93 that adjoin the porous metal layer 95, the ceramic layer 97 does not make piezoelectric displacement. In case there are a portion that is displaced and a portion that is not displaced within the device, stress would be concentrated in the border between these portions. However, presence of the ceramic layer 97 formed from a piezoelectric material in the border relieves the stress as the piezoelectric material deforms in accordance to the stress.

If the adjoining dense metal layers are connected to the external electrodes of the same polarity and a ceramic layer is disposed therebetween, the ceramic layer is subjected to strong restriction by the metal layers and exerts less stress relieving effect and allows stress concentration to occur. When at least one of the metal layers that sandwich the ceramic layer 97 is the porous metal layer 95 that has a high void ratio, as in this embodiment, on the other hand, the force of restriction becomes smaller because the contact area between the ceramic layer 97 and the porous metal layer 95 that has a high void ratio is small. Even when the stress cannot be absorbed by only the ceramic layer 97 that is sandwiched by the external electrodes of the same polarity, stress relieving effect can be improved by the cushion effect of the porous metal layer 95 that has a high void ratio.

Even when a high stress beyond expectation is generated and results in cracks of the metal layer 93 or cracks in the ceramic layer 97 sandwiched by the external electrodes of the same polarity, troubles such as short circuiting can be suppressed from occurring because the ceramic layer 97 is sandwiched by the external electrodes of the same polarity.

In this case, the porous metal layer 95 having a high void ratio functions as the electrode and two ceramic layers 97 are sandwiched by different electrodes of different polarities, so that the stress relieving effect is enhanced in accordance to the decrease in the amount of piezoelectric displacement due to the decrease of the applied voltage per thickness to one half. As a result, the multi-layer piezoelectric device having stable performance can be made.

The method for manufacturing a multi-layer piezoelectric element 91 shown in FIG. 19 will now be described. First, a powder of lead titanate zirconate (PZT), the binder described above and the plasticizer described above are mixed to form a slurry. The slurry is formed into ceramic green sheets for the ceramic layers 97, 99 by a known tape molding method such as a doctor blade method or a calender roll method.

Then a metallic paste for the metal layer 93 is prepared. The metallic paste is prepared by mixing a metal powder consisting mainly of silver palladium, a binder, a plasticizer, etc. The metallic paste is printed on one side of the ceramic green sheet by screen printing or the like. Also a metallic paste for the porous metal layer 95 having a high void ratio is prepared. This metallic paste is prepared by mixing a metal powder consisting mainly of silver, a binder, a plasticizer, etc. The metallic paste is printed on one side of the ceramic green sheet by screen printing or the like.

The green sheets having the metallic pastes printed thereon are stacked in such a structure as shown in FIG. 19 and is dried, to make the stacked compact. If the ceramic layer is required to be thicker, only a green sheet without metallic paste printed thereon may be stacked on a portion which needs to be thicker. The stacked compact may be cut into desired shape. The thickness of the metallic paste layer may be in a range from 1 to 40 μm in the case of screen printing.

After heating the stacked compact to a predetermined temperature to remove the binder, the stacked compact is fired at a temperature from 800 to 1,000° C. This causes silver to diffuse from the metal layer that has high silver concentration to the alloy layer, thus resulting in the porous metal layer 95 having a high void ratio and the metal layer 93 having relatively higher density.

After machining the sintered stack into desired dimensions, the external electrodes 101 are formed thereon. The external electrodes 101 are formed by preparing a metallic paste by mixing a metal powder consisting mainly of silver, a binder, a plasticizer, glass powder, etc., and printing the metallic paste on the side faces of the sintered stack by screen printing or the like, then firing the stack at a temperature from 600 to 800° C.

The manufacturing process may be other than that described above and may follow a known method of the prior art, except for the step in which silver diffuses from the metallic paste layer that has high silver concentration into the metallic paste layer that has low silver concentration, thus resulting in the porous metal layer 95 having a high void ratio and the metal layer 93 having relatively higher density.

Figure 21:
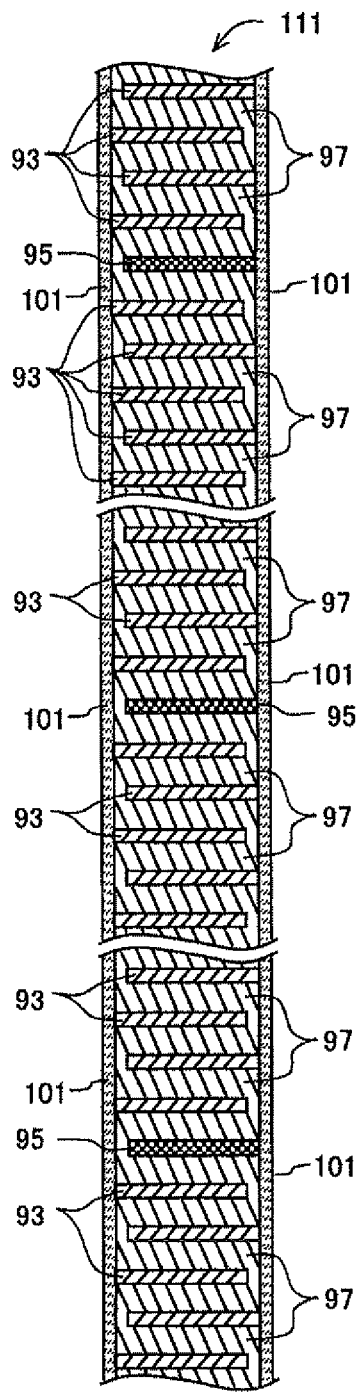
FIG. 21 is a sectional view showing a multi-layer piezoelectric device according to further another embodiment of the present invention.

FIG. 21 is a sectional view of a multi-layer piezoelectric device 111 according to further another embodiment of the present invention. As shown in FIG. 21, the multi-layer piezoelectric device 111 of this embodiment is constituted from a stack of plural metal layers 93 and plural porous metal layers 95 which are stacked via the ceramic layer 97, with a pair of external electrodes 101, 101 formed on the side faces of the stack.

In the multi-layer piezoelectric device 111, the porous metal layers 95 having a void ratio higher than that of the metal layers 93 that adjoin on both sides thereof in the stacking direction are disposed via plural metal layers 93. Plural porous metal layers 95 are disposed regularly in the stacking direction of the stack. As the porous metal layers 95 having a high void ratio are disposed via plural metal layers 93, the strength of the stack is suppressed from decreasing. Also as plural porous metal layers 95 are disposed regularly (in accordance to a predetermined rule) in the stacking direction, the stress relieving effect can be achieved evenly throughout the length in the stacking direction.

The expression that the porous metal layer are disposed regularly means, not only a case where plural porous metal layers are dispose all at the same intervals, but also a case in which the intervals between the porous metal layers are near to each other to such an extent that stress generated in the stack can be effectively distributed in the stacking direction. Specifically, the intervals between the porous metal layers are preferably within ±20%, more preferably ±15% of the mean intervals between the porous metal layers, and further more preferably the same.

The porous metal layer 95 may be constituted from plural metal lumps (lump containing layer) that are scattered between two piezoelectric material layers 97, 97 which adjoin the porous metal layer 95 in the stacking direction. The metal lumps are preferably disposed while being separated from each other by the voids. In case the porous metal layer 95 is the lump containing layer, since it is constituted from plural metal lumps that are independent from each other via the voids, the stress relieving effect is improved significantly in comparison to the case where the metal layer has a sponge-like configuration that includes a number of separate voids in the metal layer. Description of other portions will be omitted with the same reference numerals assigned as in FIG. 19.

The porous metal layer 95 of the multi-layer piezoelectric device 111 preferably has a thickness less than those of the metal layers 93, 93 that adjoin the porous metal layer 95 on both sides thereof in the stacking direction. The metal layer (porous metal layer 95) that is thinner deforms more easily than the metal layer (metal layer 93) that is thicker, and is able to absorb the stress generated by the displacement of the piezoelectric layer 97 when the metal layer deforms. As a result, the structure having the porous metal layers 95 of small thickness disposed regularly as shown in FIG. 21 can effectively absorb the stress generated by the displacement of the multi-layer piezoelectric device 111.

Preparation of the metallic paste for the porous metal layer so as to make the mass percentage X thereof higher than the mass percentage X of the metallic paste for the other metal layers makes it possible to utilize the diffusion of the metal component of the porous metal layer through the ceramic layer into the adjacent metal layer during sintering in accordance to the difference in the mass percentage X. Even when the metallic paste layers are comparable in thickness before sintering, the porous metal layer becomes thinner than the other metal layers after the metal component has diffused.

The porous metal layer 95 can be made thinner by other methods, such as forming the metallic paste layer for the porous metal layer with smaller thickness than the thickness of the metallic paste layer for the other metal layer, when printing the metallic paste layer on the ceramic green sheet.

It is preferable that the porous metal layer 95 of the multi-layer piezoelectric device 111 has higher electrical resistance than those of the metal layers 93, 93 that adjoin the porous metal layer 95 on both sides thereof in the stacking direction. The piezoelectric layer 97 that adjoins the metal layer that has high electrical resistance (the porous metal layer 95) undergoes less displacement than the piezoelectric layer 97 that adjoins the metal layer that has low electrical resistance (the metal layer 93). This constitution having plural piezoelectric layers 97 that undergo smaller displacement and are disposed in the multi-layer piezoelectric device 111 makes it possible to distribute the stress generated by the displacement, thereby suppressing troubles such as cracks from occurring.

Electrical resistance of the porous metal layer 95 can be made higher than those of the other metal layers 93 by several methods. For example, a cross sectional area of the porous metal layer 95 may be made smaller than those of the other metal layers 93. Specifically, the cross sectional area can be made smaller by making the layer thinner or making the void ratio higher. Alternatively, a material having higher resistivity may be used to form the porous metal layer 95.

It is also preferable that the porous metal layer 95 of the multi-layer piezoelectric device 111 has higher mass percentage Y than that of the metal layers 93 that adjoin therewith on both sides in the stacking direction. It is particularly preferable that mass percentage Y peaks in the porous metal layer 95 and gradually decreases from the porous metal layer 95 over at least two metal layers 93 on both sides in the stacking direction.

The multi-layer piezoelectric device 111 having such a structure has an advantage of high strength to endure thermal shock since concentration of the metal component decreases gradually through plural metal layers. This is due to the fact that the metal has higher heat conductivity than the ceramics, and that heat conductivity changes with the composition of the metal component. That is, as concentration of the metal component decreases gradually through plural metal layers, heat conductivity in the ceramic member can be suppressed from changing abruptly.

Figure 22:
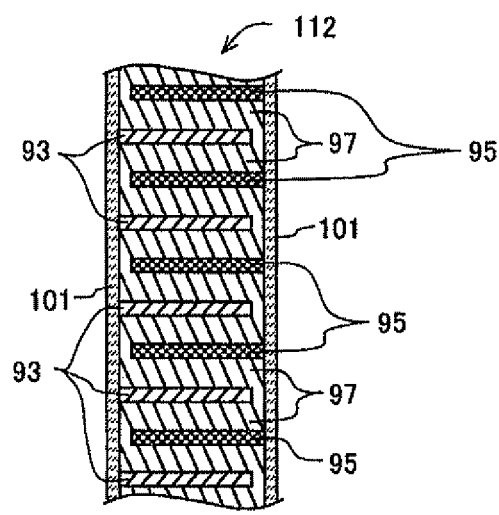
FIG. 22 is a sectional view showing a multi-layer piezoelectric device according to further another embodiment of the present invention.

FIG. 22 is a sectional view of a multi-layer piezoelectric device 112 according to further another embodiment of the present invention. As shown in FIG. 22, the multi-layer piezoelectric device 112 is constituted from the porous metal layers 95 and the metal layers 93 other than the porous metal layer 95 that are stacked alternately one on another. Thus each of the piezoelectric layers 97 is sandwiched by the porous metal layer 95 and the metal layer 93. As every piezoelectric layer 97 that undergoes piezoelectric displacement is in contact with the porous metal layer 95 that has a high stress relieving effect, the stress relieving effect can be enhanced further. Presence of the porous metal layers and the dense metal layers that are disposed alternately one on another makes it possible to apply voltage via the metal layer 93 to the piezoelectric layer 97 so as to undergo piezoelectric displacement.

The porous metal layer 95 disposed on the opposite side of the piezoelectric layer 97 is porous and is therefore weak in the force of clamping the piezoelectric layer 97, thus generating less stress. As a result, the piezoelectric layer 97 is virtually free of clamping force, and is capable of generating a large displacement while mitigating the stress generated between the metal layer 93 and the piezoelectric layer 97.

In the multi-layer piezoelectric device 112 where the porous metal layer 95 is used as the internal electrode, void ratio in the porous metal layer 95 is preferably in a range from 7% to 70%. By controlling the void ratio to not higher than 70%, electrical conductivity of the porous metal layer 95 can be suppressed from decreasing, so as to put the adjacent piezoelectric layer in electric field of sufficient intensity and cause it to undergo a large amount of displacement. By controlling the void ratio to not lower than 7%, on the other hand, it is made possible to suppress the bonding strength of the piezoelectric layer that adjoins the porous metal layer 95 from becoming too strong. As a result, cracks are likely to occur in the interface between the porous metal layer 95 and the piezoelectric layer 97 during operation, thereby suppressing the cracks from occurring in the piezoelectric layer.

In order to increase the insulation property of the porous metal layer 95, the void ratio in the porous metal layer 95 is preferably in a range from 24% to 98%, more preferably from 24 to 90%. This enables it to achieve higher insulation, less clamping force of the metal layer exerted on the piezoelectric layer and less stress generated during operation.

In order to increase the amount of displacement of the piezoelectric layer, the void ratio is preferably in a range from 50% to 90%. In order to utilize the thermal insulation effect and of air in the voids and improve the resistance to thermal shock of the multi-layer piezoelectric device, the void ratio is more preferably in a range from 70% to 90%. To achieve a higher insulation, the void ratio is more preferably 70% or higher.

The void ratio of the metal layers other than the porous metal layer is preferably in a range from 0.1% to 40% in order to achieve high electrical conductivity and efficiently apply voltage to the piezoelectric layer. In order to increase the electrical conductivity further and cause the piezoelectric layer to undergo larger displacement, the void ratio is more preferably in a range from 0.1% to 20%.

In the multi-layer piezoelectric device 112, it is preferable that the porous metal layers 95 are disposed on both ends of plural metal layers in the stacking direction. In the multi-layer piezoelectric device 112, high stress is likely to be generated in the interface with the ceramic layer (inactive layer) 99. Therefore, it is preferable to use the in the porous metal layer 95 for the metal layer that adjoins the ceramic layer 99. Furthermore it is preferable to make the void ratio in the porous metal layer 95 that adjoins the ceramic layer 99 higher, among plural porous metal layers 95.

In the multi-layer piezoelectric device 112, the porous metal layer 95 is preferably used as the positive electrode. The interface between the piezoelectric layer and the metal layer where stress tends to concentrate is subject to localized deformation caused by local concentration of electric field due to the edge effect. At the same time, phase transition in the crystal structure of the piezoelectric layer may occur due to the stress, thus resulting in local heating. When the partial pressure of oxygen associated with the oxygen ions of the piezoelectric layer due to this heat is higher than the partial pressure of oxygen around the multi-layer piezoelectric device, oxygen holes that transmit the ions may be generated locally in the piezoelectric layer, thus causing the characteristics of the multi-layer piezoelectric device to change.

Moreover, since the ionized oxygen hole has negative charge, migration of the ionized oxygen hole is more likely to occur in the metal layer on the positive electrode side than on the negative electrode side. Accordingly, supply of oxygen to the portion around the piezoelectric layer can be increased by increasing the void ratio in the metal layer on the positive electrode side, so that the generation of oxygen holes is suppressed and durability can be suppressed from decreasing.

Figure 23:
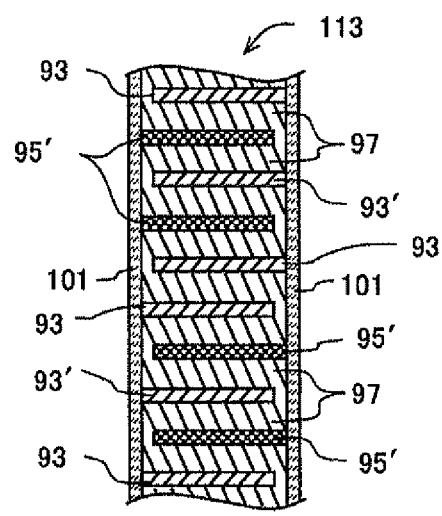
FIG. 23 is a sectional view showing a multi-layer piezoelectric device according to further another embodiment of the present invention.

FIG. 23 is a sectional view of a multi-layer piezoelectric device 113 according to further another embodiment of the present invention. As shown in FIG. 23, the multi-layer piezoelectric device 113 is constituted from plural metal layers that include metal component $M_1$ that are stacked one on another via the piezoelectric layer 97. The plurality of metal layers include plural dense metal layers 93' that have less voids than the metal layers 95' that adjoin therewith on both sides thereof in the stacking direction. The metal layers 95' are porous metal layers.

When the device has only one porous metal layer 95' that has a high stress relieving effect, stress generated in the device tends to concentrate around the porous metal layer 95'. Since the piezoelectric layer 97 that contacts the metal layer 93 adjacent to the porous metal layer 95' undergoes displacement, stress is likely to concentrate in the piezoelectric layer that is disposed between the metal layer 93 adjacent to the porous metal layer 95' and the device surface.

This stress concentration can be mitigated by sandwiching the piezoelectric layer that is disposed between the metal layer 93 and the device surface with the porous metal layer 95' that have high stress relieving effect. Moreover, very high stress relieving effect can be achieved since two stress relieving layers (porous metal layers 95') disposed near to each other cooperate to achieve the effect.

In addition, in such a constitution as shown in FIG. 23 where polarity of the external electrodes connected to the dense metal layer 93' that is sandwiched by the porous metal layers 95' is changed alternately in the stacking direction of the device, the stress generated by the clamping force of the external electrodes exerted on the dense metal layer 93' can be uniformly distributed. This constitution further improves the stress relieving effect.

In the multi-layer piezoelectric device of the present invention, it is preferable that the two first metal layers that adjoin the second metal layer on both sides thereof in the stacking direction are connected to the external electrodes of different polarities, so that the stress generated in the stack can be effectively absorbed by the second metal layer during operation of the device. In case the second metal layer is disposed between two piezoelectric layer that are sandwiched by the adjoining internal electrodes of the same polarity, the piezoelectric layer that adjoins the second metal layer does not undergo displacement when voltage is applied to the internal electrode. In case the second metal layer is disposed between two internal electrodes of the same polarity, stress tends to concentrate in the border between a portion that undergoes displacement and a portion that does not undergo displacement. Such a stress concentration does not occur when the second metal layer is sandwiched by the internal electrodes of different polarities.

Figure 24A:
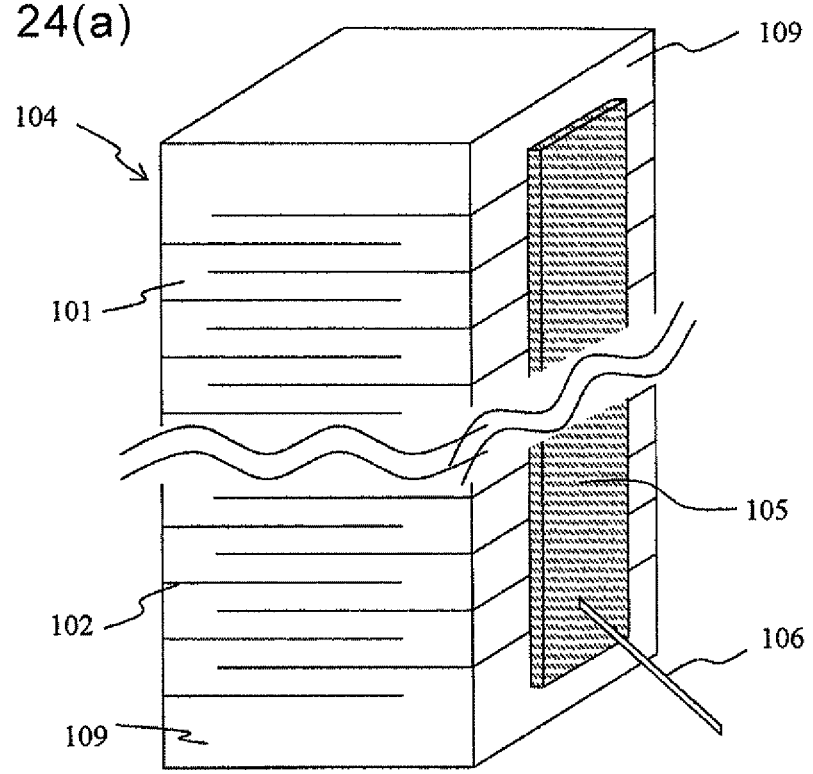
FIG. 24($a$) is a perspective view showing a multi-layer piezoelectric device according to further another embodiment of the present invention, and FIG. 24($b$) is a partial perspective view explanatory of the state of piezoelectric layers and internal electrode layers being stacked in the multi-layer piezoelectric device.
Figure 24B:
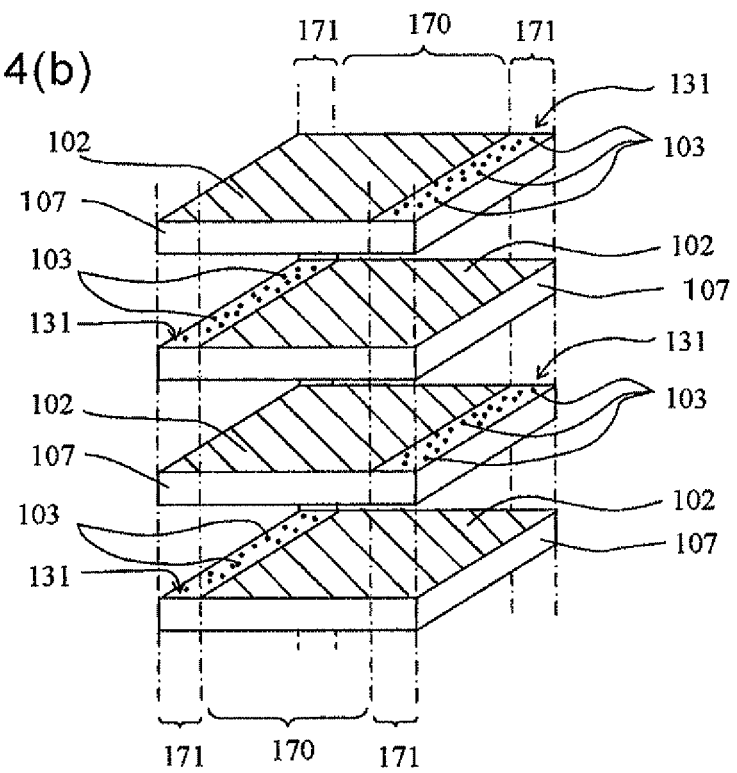

FIG. 24(a) is a perspective view showing the multi-layer piezoelectric element according to this embodiment. FIG. 24(b) is a partial sectional view showing the state of the piezoelectric layers and the internal electrode layers (metal layers) being stacked in the multi-layer piezoelectric element.

As shown in FIG. 24(a) and FIG. 24(b), the multi-layer piezoelectric device has a stack 104 formed by stacking plural piezoelectric layers 107 via internal electrode layers 102. The stack 104 has, formed on the side face thereof, a pair of external electrodes 105 that are connected to plural internal electrode layers 102 in every other layer. The plurality of internal electrode layers 102 are not formed over the entire principal surface of the piezoelectric layer 107, so that the so-called partial electrode structure is formed where the internal electrode layer 102 has a surface area smaller than the area of the principal surface of the piezoelectric layer 107. The internal electrode layers 102 are exposed alternately on either of the opposing side faces of the stack 104.

In this multi-layer piezoelectric device, since the internal electrode layers 102 are formed in the partial electrode structure as described above, when a voltage is applied across the external electrodes 105, 105, only the portion of the piezoelectric layer 107 that is interposed between two internal electrode layers 102 from above and below, namely the region where one of the internal electrode layers 102 overlaps the other internal electrode layer 102 in the stacking direction (displacement portion 170), undergoes displacement. The piezoelectric layer 107 does not undergo displacement in the portion thereof where the internal electrode layer 102 is not formed (peripheral area 131) as shown in FIG. 24(b) (undisplaceable portion 171).

In case the multi-layer piezoelectric device of the present invention is used as a piezoelectric actuator, lead wires 106 are connected to the external electrodes 105 by soldering, with the lead wires 106 being connected to an external voltage source. When a predetermined voltage is applied across the pair of external electrodes 105, 105 from the external voltage source via the lead wires 106, the piezoelectric layers 107 undergo displacement due to reverse piezoelectric effect.

As shown in FIG. 24(b), the multi-layer piezoelectric device has plural peripheral areas 131 located between the two piezoelectric layers 107, 107, that are disposed consecutively in the stacking direction, and located between the edge 102a of the internal electrode layer 102 and the side face 104a of the stack 104. In the multi-layer piezoelectric element of this embodiment, an area where plural metal lumps (partial metal layer) 103 are dispersed is formed in the peripheral areas 131, that is disposed between the piezoelectric layer 107 and the piezoelectric layer 107 among plural peripheral areas 131.

As shown in FIG. 24(b), the metal lumps 103 are scattered over almost the entire peripheral areas 131. Instead of the metal lumps 103, other material that can deform more easily than the piezoelectric ceramics may be scattered. The word "deformation" here covers any type of deformation such as elastic deformation, plastic deformation and brittle deformation.

Figure 25:
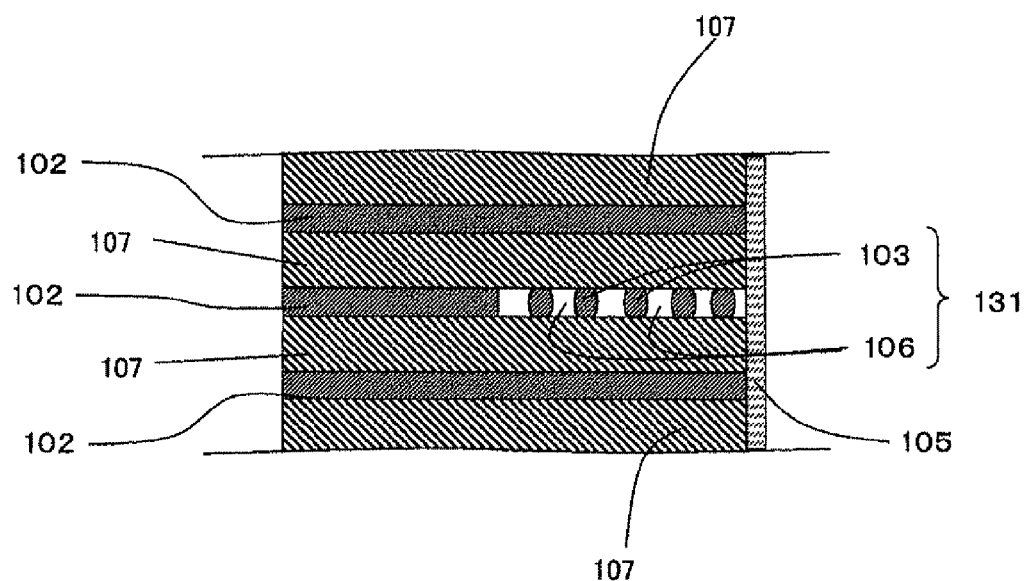
FIG. 25 is a sectional view showing a peripheral portion of the device shown in FIG. 24.

The metal lumps 103 in this embodiment are formed from a metal as described above. The metal lumps 103 are scattered in the peripheral areas 131 while being isolated from the internal electrode 102. The phrase "scattered while being isolated from the internal electrode 102" means that plural metal lumps 103 are not in electrical continuity with the internal electrodes 102 and the metal lumps 103 are also isolated from each other so as not in electrical continuity with each other (FIG. 25).

There is no restriction on the position in the stack 104 where the metal lumps 103 are to be dispersed, among plural peripheral areas 131 included in the stack 104. For example, the metal lumps 103 may be scattered in all of the peripheral areas 131 (the peripheral areas 131 that adjoin all of the internal electrode layers 102), or the metal lumps 103 may be scattered in arbitrarily selected peripheral areas 131. In this embodiment, there are plural peripheral areas 131 wherein the metal lumps 103 are scattered, and the peripheral areas 131 are disposed at intervals of two or more piezoelectric layers 107 in the stacking direction of the stack 104.

The metal lumps 103 may be formed from the same material as that used to form the internal electrode layer 102, and are preferably formed from a silver-palladium alloy. The silver-palladium alloy is a pliable metal that deforms relatively easily among metals, and therefore even a low content thereof can reduce the restrictive force of the undisplaceable portion. The silver-palladium alloy is also resistant to fatigue and has high resistance against oxidization, and is therefore capable of suppressing the durability of the multi-layer piezoelectric device from deteriorating. There are no restrictions on the shape and size of metal the lumps 103 and on the number of the metal lumps 103 formed in the peripheral area 131. Minimum requirement is that the metal lumps 103 are scattered as described above.

Specifically, the proportion of the total area of the metal lumps 103 to the area of the peripheral area 131, when the peripheral area 131 having the metal lumps 103 scattered therein is viewed in the stacking direction of the stack 104, is preferably from 0.1 to 50%, more preferably from 5 to 30%.

When the proportion of the area occupied by the metal lumps 103 is not less than 0.1%, the effect of reducing the restrictive force of restricting the displacement of the displacement portion is obtained. When the proportion of the metal lumps 103 is not more than 50%, the strength against breakage and the insulation capability can be suppressed from decreasing.

There is no restriction on the maximum size r of the metal lumps 103 viewed in the stacking direction of the stack 104. The maximum size r of the metal lumps 103 is preferably not larger than one half and more preferably not larger than one tenth of the minimum distance L between the internal electrode layer 102 and the external electrode 105 in the peripheral area 131. For example, in case the minimum distance L is about 1 mm, maximum size r of the region 3 is preferably 500 µm or less, more preferably 100 µm or less, which enables it to maintain the strength against breakage and the insulation capability at appropriate levels.

In this embodiment, the peripheral area 131 where the metal lumps 103 are scattered includes insulating ceramics regions in part or the entire area between adjoining metal lumps 103, so that the insulating ceramics regions connect the adjoining piezoelectric layers 107, 107 together. While there is no restriction on the kind of ceramic material that is disposed between the adjoining metal lumps 103 and connects the adjoining piezoelectric layers 107, 107 together, it is preferably the same material as that of the piezoelectric layers 107.

In case lead titanate zirconate is used as the material to form the piezoelectric layers 107, it is preferable to use lead titanate zirconate as the insulating ceramic material that connects the piezoelectric layers 107 together in the peripheral area 131. This enables it to prevent the occurrence of troubles arising from the difference in thermal expansion and achieve higher bonding strength between the piezoelectric layers 107.

The peripheral areas 131 where the metal lumps 103 are scattered are preferably disposed at equal intervals in the stacking direction of the stack 104. Specifically, it is preferable that plural metal lumps 103 are scattered in plural peripheral areas 131, that are located between the edges 102a of plural internal electrode layers 102 located at equal intervals via two or more piezoelectric layers 107, which are selected from among plural piezoelectric layers 102, and the side face 104a of the stack 104. As the metal lumps 103 are scattered in plural peripheral areas 131 that are selected so as to be located at equal intervals, displacement performance, it is made possible to set the displacement performance and strength against breakage in a more well-balanced manner.

There is no restriction on the kind of material of the piezoelectric layer 107, for which various piezoelectric ceramics materials may be used. For example, a Bi layered compound (perovskite type layered compound), a tungsten bronze type compound, an Nb-based perovskite type compound (niobate alkaline compound (NAC) such as sodium niobate), an niobate alkaline earth compound (NAEC) such as barium niobate, lead magnesium niobate (PMN), lead nickel niobate (PNN), lead titanate zirconate (PZT) containing Pb, lead titanate or other perovskite type compound may be used.

Among these, a perovskite type compound containing at least lead is preferably used. For example, it is preferable to use a material containing lead magnesium niobate (PMN), lead nickel niobate (PNN), lead titanate zirconate (PZT) containing Pb or lead titanate. Among these, lead titanate zirconate or lead titanate is preferably used in particular, in order to achieve a large amount of displacement. The piezoelectric ceramic material preferably has a high value of piezoelectric strain constant $d_{33}$ which represents the piezoelectric characteristic.

The internal electrode layer 102 may be formed from such materials as gold, silver, palladium, platinum, copper, aluminum or an alloy thereof. As an alloy, for example, a silver-palladium alloy may be used. The thickness of the internal electrode layer 102 should be such that ensures electrical conductivity and does not impede displacement, and is generally in a range from about 0.5 to 7 µm, and preferably from about 1 to 5 µm.

The thickness of the piezoelectric layer 1, namely the distance between the internal electrode layers 2 is preferably in a range from about 50 to 200 µm. When the piezoelectric layer 107 has a thickness in the range described above, the actuator can be made in compact and low-profile construction, and insulation breakdown can be suppressed from occurring. The external electrodes 105 may be formed from such materials as gold, silver, palladium, platinum, copper, aluminum, nickel or an alloy thereof.

Then a silver powder, a glass powder and a binder are mixed to prepare an electrically conductive silver-glass paste in order to make the multi-layer piezoelectric device from the ceramic member of this embodiment. The electrically conductive paste is printed on the opposing side faces 104a, 104a of the stack 104 by a method such as screen printing or the like and is, after being dried, baked at a temperature in a range from 500 to 800° C. thereby forming the external electrodes 105. Instead of printing, a sheet with thickness of 5 µm or less formed by drying the silver-glass paste may be bonded by baking.

Then the stack 4 having the external electrodes 105 formed thereon is dipped in a silicone rubber solution. After deaerating the silicone rubber solution in vacuum, the stack 104 is pulled out of the silicone rubber solution with the side faces of the stack 104 being coated with the silicone rubber. Then the silicone rubber coating on the side faces of the stack 104 is hardened so as to complete the multi-layer piezoelectric device of this embodiment.

Last, lead wires are connected to the external electrodes 105, and DC voltage of 3 kV/mm is applied across the pair of external electrodes 105 via the lead wires so as to apply polarization treatment to the stack 104, thereby to complete the piezoelectric actuator that employs the multi-layer piezoelectric device of the present invention. The lead wires are connected to an external voltage source that supplies the voltage via the lead wires and the external electrodes 105 to the metal layers 102, so that the piezoelectric layers 107 undergo significant displacement due to reverse piezoelectric effect. Thus the device functions as, for example, an automobile fuel injection valve that injects fuel to an engine.

Injection Apparatus

Figure 27:
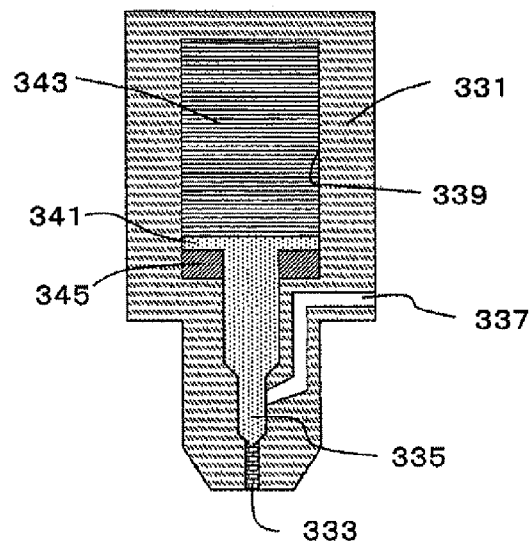
FIG. 27 is a sectional view showing an injection device according to one embodiment of the present invention.

FIG. 27 is a schematic sectional view of an injection apparatus according one embodiment of the present invention. As shown in FIG. 27, the injection apparatus of this embodiment has the multi-layer piezoelectric device of the present invention represented by the embodiments described above in a container 331 that has an injection hole 333 formed at one end thereof. The container 331 includes a needle valve 335 capable of opening and closing the injection hole 333 disposed therein.

The injection hole 333 is connected to a fuel passage 337 that is capable of communicating therewith in response to the motion of the needle valve 335. The fuel passage 337 is connected to a fuel source provided outside, so that a fuel is supplied through the fuel passage 337 at a high pressure that remains constant. Accordingly, when the needle valve 335 opens the injection hole 333, the fuel supplied to the fuel passage 337 is injected at a high constant pressure into a fuel chamber of an internal combustion engine which is not shown.

The needle valve 335 has a top end that has a larger inner diameter, and a piston 341 is disposed so as to be capable of sliding in a cylinder 339 that is formed in the container 331. The piezoelectric actuator 343 having the multi-layer piezoelectric device described above is housed in the container 331.

With such an injection apparatus as described above, when the piezoelectric actuator 343 is caused to expand by applying a voltage thereto, the piston 341 is pressed so that the needle valve 335 plugs the injection hole 333 and shuts off the fuel supply. When the voltage is removed, the piezoelectric actuator 343 contracts and a Belleville spring 345 presses back the piston 341 so that the injection hole 333 communicates with the fuel passage 337 thereby allowing the fuel to be ejected.

The injection apparatus of the present invention may also be constituted from the container having the injection hole and the multi-layer piezoelectric device described above, so that the liquid that fills the container is discharged through the injection hole by the operation of the multi-layer piezoelectric device. That is, the device may not necessarily be disposed in the container. The only requirement is that pressure is applied to the inside of the container by the operation of the multi-layer piezoelectric device. In the present invention, the liquid includes fuel, ink and various other liquids such as electrically conductive paste.

Fuel Injection System

Figure 28:
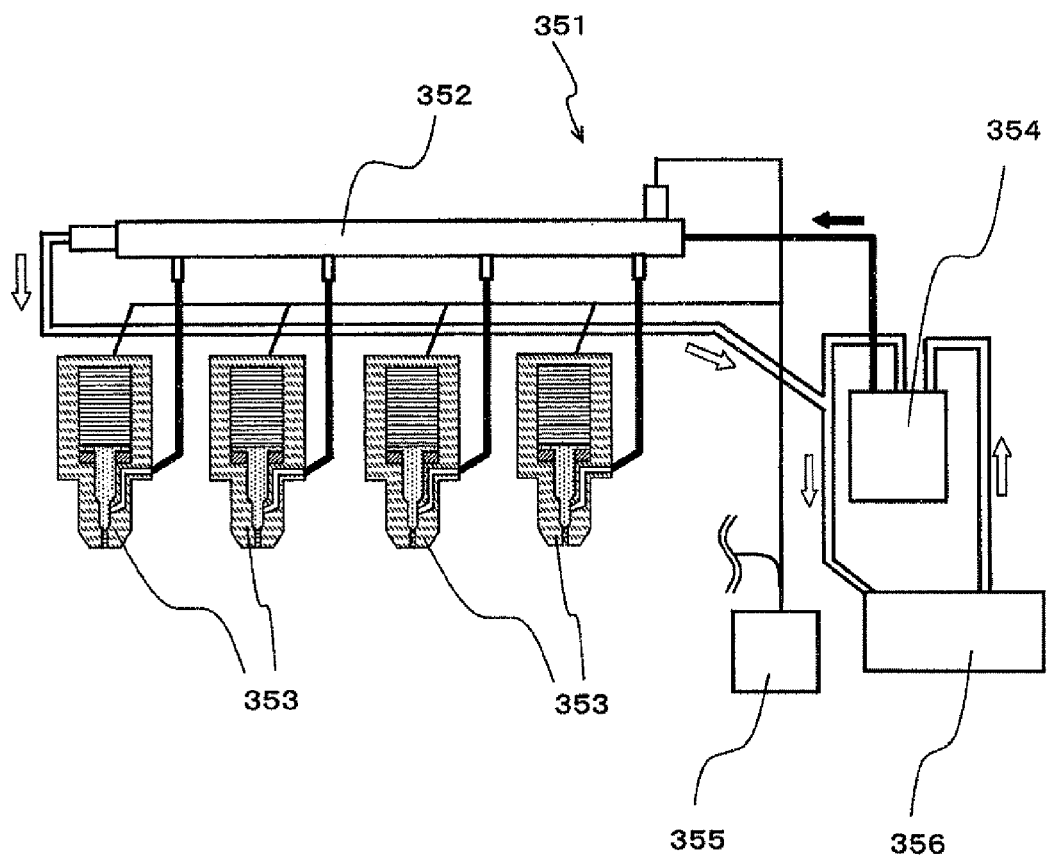
FIG. 28 is a schematic diagram showing a fuel injection system according to one embodiment of the present invention.

FIG. 28 is a schematic diagram showing a fuel injection system according to one embodiment of the present invention. As shown in FIG. 28, the fuel injection system 351 of this embodiment comprises a common rail 352 that stores a high-pressure fuel, plural injection apparatuses 353 that eject the fuel stored in the common rail 352, a pump 354 that supplies the high-pressure fuel to the common rail 352 and an injection control unit 355 that sends a drive signal to the injection apparatus 353.

The injection control unit 355 controls the quantity of fuel to be injected and the timing of injection while monitoring the condition inside of the engine combustion chamber by means of sensor or the like. The pump 354 boosts the pressure of the fuel to a level from about 1,000 to 2,000 qtm, preferably from about 1,500 to 1,700 qtm, and supplies the fuel to the common rail 352.

The common rail 354 stores the fuel that is supplied from the pump 354, and sends it to the injection apparatus 353 as required. The injection apparatus 353 injects a small amount of fuel through the injection hole 333 in the form of mist into the combustion chamber.

Example 1

Gas Sensor

A gas sensor device comprising a ceramic member of the present invention was manufactured as follows. First, a zirconia powder consisting mainly of a stabilized zirconia (5 mol % $Y_2O_3$-containing $ZrO_2$) powder having a mean particle size of 0.4 µm, a glass powder, a binder, and a plasticizer were mixed to prepare a slurry. The slurry was formed into a ceramic green sheet having a thickness of 150 µm by a doctor blade method.

Then, on one surface of the ceramic green sheet, an electrically conductive paste prepared by adding a binder to a raw powder such as a silver alloy powder with the composition shown in Table 1 was printed in a thickness of 30 µm using a screen printing method. At this time, with respect to the portion to be provided with a heating element, a heating element pattern was printed in the shape of a folded zigzag shape. Then, the respective green sheets were stacked to obtain a stacked compact having a shape shown in FIG. 14. Regarding the position where a predetermined thickness of a ceramic layer is required, a required number of only green sheets were stacked without printing the electrically conductive paste.

After heating the stacked compact to a predetermined temperature to remove the binder, the stacked compact was fired at a temperature from 800 to 1,200° C. to obtain a sintered stack. Therefore, when the metal layers with a difference in silver concentration are formed via a ceramic layer, silver diffused from the metal layer having a high concentration to the metal layer having a low concentration to form a porous metal layer 47 having a high void ratio, and thus a comparatively dense metal layer 53 was formed.

In order to form a metal layer 45 having a high void ratio having a structure shown in FIG. 14, a metal powder consisting mainly of platinum having a mean particle size of 1 μm, a binder, and a plasticizer were mixed to prepare an electrically conductive paste. The electrically conductive paste was applied on the portion to be provided with the metal layer 45 of the above sintered stack by screen printing. When fired at a temperature from 800 to 1,000° C., a dense ceramic layer can be obtained by sintering. However, platinum having a higher liquidus point than that of ceramics is not converted into a dense sintered stack and a metal layer 45 having a high void ratio is formed.

After machining the sintered stack into desired dimensions, external electrodes were formed thereon. First, a metal powder consisting mainly of silver, a binder, a plasticizer and a glass powder were mixed to prepare an electrically conductive paste for an external electrode. The electrically conductive paste was screen-printed on the side faces of the sintered stack. Then, the sintered stack was fired at a temperature from 600 to 800° C. to form an external electrode 49, and thus a heater-integrated oxygen sensor was obtained.

The temperature of the gas sensor device was maintained at a temperature of 700° C. by applying a voltage to the heater. Then, a mixed gas of hydrogen, methane, nitrogen and oxygen at an air fuel ratio of 12 was sprayed over the sensor, and thus it was confirmed whether or not the sensors functions by the fact whether or not a electromotive force is generated by the sensor. After alternately spraying a mixed gas of an air fuel ratio of 12 and a mixed gas of an air fuel ratio of 23 $1\times10^9$ times at intervals of 0.5 seconds, it was confirmed that the electromotive force varies depending on a difference in the air fuel ratio. Then, after spraying a mixed gas at an air fuel ratio of 12 over the sensor, it was confirmed whether or not the electromotive force is generated by the sensor. The results are shown in Table 1.

in the mass percentage of the metallic paste layer is large. In particular, samples Nos. 3, 5, 6, 10 and 11, in which a mass percentage X of silver of metal layers 45 and 47 is 90% or more and a difference in the mass percentage is from 3 to 5%, showed most excellent durability.

Example 2

Fuel Cell

A fuel cell device comprising a ceramic member of the present invention was manufactured as follows. First, a zirconia powder consisting mainly of a cordierite (5 mol % $Y_2O_3$-containing $ZrO_2$) powder having a mean particle size of 0.4 μm, a glass powder, a binder, and a plasticizer were mixed to prepare a slurry. The slurry was formed into a ceramic green sheet having a thickness of 150 μm by a doctor blade method.

On one surface of the ceramic green sheet, an electrically conductive paste prepared by adding a binder to a raw powder such as a silver alloy powder with the composition shown in Table 2 was printed in a thickness of 30 μm using a screen printing method. Then, the respective green sheets were stacked to obtain a stacked compact having a shape shown in FIG. 17. Regarding the position where a predetermined thickness of a ceramic layer is required, a required number of only green sheets were stacked without printing the electrically conductive paste.

After heating the stacked compact to a predetermined temperature to remove the binder, the stacked compact was fired at a temperature from 800 to 1,200° C. to obtain a sintered stack. Therefore, when the metal layers with a difference in silver concentration are formed via a ceramic layer, silver diffused from the metal layer having a high concentration to the metal layer having a low concentration to form metal layers 63, 65 having a high void ratio, and thus comparatively dense metal layers 73, 77 were formed.

After machining the sintered stack into desired dimensions, external electrodes are formed thereon. First, a metal powder consisting mainly of silver, a binder, a plasticizer and

TABLE 1

| No. | Metal composition of second metallic paste layer (high-content metallic pate layer) | Metal composition of first metallic paste layer | Metal composition of second metal layer after firing | Void ratio of second metal layer after firing (%) | Metal composition of first metal layer after firing | Void ratio of first metal layer after firing (%) | Electro-motive force (V) | Electromotive force after $1 \times 10^9$ cycles (V) |
|---|---|---|---|---|---|---|---|---|
| 1 | 100% Ag | 100% Ag | 100% Ag | 25 | 100% Ag | 25 | 0 | None |
| 2 | 100% Ag | 99% Ag—1% Pt | 100% Ag | 70 | 99.5% Ag—0.5% Pd | 15 | 0.5 | 0.3 |
| 3 | 100% Ag | 97% Ag—3% Pt | 97% Ag—3% Pt | 85 | 97% Ag—3% Pt | 10 | 0.65 | 0.65 |
| 4 | 97% Ag—3% Pt | 95% Ag—5% Pt | 96% Ag—4% Pt | 75 | 96% Ag—4% Pt | 10 | 0.7 | 0.65 |
| 5 | 98% Ag—2% Pt | 95% Ag—5% Pt | 95% Ag—5% Pt | 85 | 95% Ag—5% Pt | 10 | 0.65 | 0.65 |
| 6 | 95% Ag—5% Pt | 90% Ag—10% Pt | 92% Ag—8% Pt | 80 | 91% Ag—9% Pt | 15 | 0.7 | 0.7 |
| 7 | 95% Ag—5% Pt | 85% Ag—15% Pt | 90% Ag—10% Pt | 75 | 86% Ag—14% Pt | 15 | 0.65 | 0.6 |
| 8 | 95% Ag—5% Pt | 75% Ag—25% Pt | 85% Ag—15% Pt | 65 | 80% Ag—20% Pt | 20 | 0.6 | 0.4 |
| 9 | 95% Ag—5% Pt | 65% Ag—35% Pt | 75% Ag—25% Pt | 60 | 70% Ag—30% Pt | 20 | 0.55 | 0.43 |
| 10 | 98% Ag—2% Pd | 95% Ag—5% Pd | 95% Ag—5% Pd | 85 | 95% Ag—5% Pd | 10 | 0.65 | 0.65 |
| 11 | 98% Ag—2% Pt | 95% Ag—5% Pd | 95% Ag—5% Pt | 85 | 95% Ag—5% Pd | 10 | 0.65 | 0.65 |

As is apparent from the results shown in Table 1, since sample No. 1 comprising a dense metal layer 47 cannot supply the air to a ceramic layer 43 as a solid electrolyte that enables the sensor to function via the metal layer 47, no electromotive force was generated and the sample did not function as an oxygen sensor. Samples Nos. 2 to 11 functioned as an oxygen sensor. As a result, it was found that samples show excellent durability when a mass percentage of silver of a metallic paste layer is 85% or more and a difference a glass powder were mixed to prepare an electrically conductive paste for an external electrode. The electrically conductive paste was screen-printed on the side faces of the sintered stack. Then, the sintered stack was fired at a temperature from 600 to 800° C. to form an external electrode, and thus a fuel cell device was obtained.

Oxygen was supplied to an air pole side and hydrogen was supplied to a fuel pole side, and then power density of power generation was measured at a state of being maintained at 800° C. A continuous operation was conducted at 800° C. for 1,000 hours and power density of power generation was measured again. The results are shown in Table 2.

order to form a porous electrode for comparison of performances, a metal paste prepared by adding the same amount of acryl beads having a mean particle size of 5 μm to a platinum

TABLE 2

| No. | Metal composition of second metallic paste layer (high-content metallic pate layer) | Metal composition of first metallic paste layer | Metal composition of second metal layer after firing | Void ratio of second metal layer after firing (%) | Metal composition of first metal layer after firing | Void ratio of first metal layer after firing (%) | Gas flow rate (mW/cm²) | Gas flow rate after 1,000 hrs. (mW/cm²) |
|---|---|---|---|---|---|---|---|---|
| 1 | 100% Ag | 100% Ag | 100% Ag | 25 | 100% Ag | 25 | 0 | None |
| 2 | 100% Ag | 99% Ag—1% Pt | 100% Ag | 70 | 99.5% Ag—0.5% Pd | 15 | 2 | 1 |
| 3 | 100% Ag | 97% Ag—3% Pt | 97% Ag—3% Pt | 85 | 97% Ag—3% Pt | 10 | 2.6 | 2.6 |
| 4 | 97% Ag—3% Pt | 95% Ag—5% Pt | 96% Ag—4% Pt | 75 | 96% Ag—4% Pt | 10 | 2.5 | 2.4 |
| 5 | 98% Ag—2% Pt | 95% Ag—5% Pt | 95% Ag—5% Pt | 85 | 95% Ag—5% Pt | 10 | 2.6 | 2.6 |
| 6 | 95% Ag—5% Pt | 90% Ag—10% Pt | 92% Ag—8% Pt | 80 | 91% Ag—9% Pt | 15 | 2.7 | 2.7 |
| 7 | 95% Ag—5% Pt | 85% Ag—15% Pt | 90% Ag—10% Pt | 75 | 86% Ag—14% Pt | 15 | 2.6 | 2.5 |
| 8 | 95% Ag—5% Pt | 75% Ag—25% Pt | 85% Ag—15% Pt | 65 | 80% Ag—20% Pt | 20 | 2.6 | 1.5 |
| 9 | 95% Ag—5% Pt | 65% Ag—35% Pt | 75% Ag—25% Pt | 60 | 70% Ag—30% Pt | 20 | 2.7 | 1.3 |
| 10 | 98% Ag—2% Pd | 95% Ag—5% Pd | 95% Ag—5% Pd | 85 | 95% Ag—5% Pd | 10 | 2.6 | 2.6 |
| 11 | 98% Ag—2% Pt | 95% Ag—5% Pd | 95% Ag—5% Pt | 85 | 95% Ag—5% Pd | 10 | 2.6 | 2.6 |

As is apparent from the results shown in Table 2, since sample No. 1 comprising metal layers 63, 65 as a dense electrode layer can supply neither oxygen nor hydrogen to ceramic layer 67 as a solid electrolyte that enables a powder generation function via metal layers 63, 65, no electromotive force was generated and the sample did not function as a fuel cell. Samples Nos. 2 to 11 functioned as a fuel cell. As a result, it was found that samples show excellent durability when a mass percentage X of silver of a metallic paste layer is 85% or more and a difference in the mass percentage of the metallic paste layer is large. In particular, samples Nos. 3, 5, 6, 10 and 11, in which a mass percentage X of silver of the metallic paste layer is 90% or more and a difference in the mass percentage is from 3 to 5%, showed most excellent durability.

Example 3

Multi-Layer Piezoelectric Device

A multi-layer piezoelectric device comprising a ceramic member of the present invention was manufactured as follows. First, a raw powder consisting mainly of a lead titanate zirconate (PZT) powder having a mean particle size of 0.4 μm, a binder, and a plasticizer were mixed to prepare a slurry. The slurry was formed into a ceramic green sheet having a thickness of 150 μm by a doctor blade method. On one surface of the ceramic green sheet, an electrically conductive paste prepared by adding a binder to a raw powder such as a silver alloy powder with the composition shown in Table 3 was printed in a thickness of 30 μm using a screen printing method. To a metallic paste layer for forming a lump containing layer 95, a lead titanate zirconate (PZT) powder having a mean particle size of 0.4 μm was added in the amount of 1% by mass based on the metal powder.

Then, green sheets were stacked to obtain a stacked compact having a shape shown in FIG. 19. Regarding the operation region, 100 metal layers were stacked. Regarding the position where a predetermined thickness of a ceramic layer is required, a required number of only green sheets were stacked without printing the electrically conductive paste. In powder having a mean particle size of 10 μm was used to form a porous electrode (sample No. 32). In order to form a dense electrode, a silver-palladium alloy layer having a thickness of 1 μm was formed using a sputtering method (sample No. 33).

After heating the stacked compact to a predetermined temperature to remove the binder, the stacked compact was fired at a temperature from 800 to 1,200° C. to obtain a sintered stack. Therefore, when the metal layers with a difference in silver concentration are formed via a ceramic layer, silver diffused from the metal layer having a high concentration to the metal layer having a low concentration to form a porous metal layer 95 having a high void ratio, and thus a comparatively dense metal layer 93 was formed.

After machining the sintered stack into desired dimensions, external electrodes are formed thereon as follows. First, a metal powder consisting mainly of silver, a binder, a plasticizer and a glass powder were mixed to prepare an electrically conductive paste for an external electrode. The electrically conductive paste was screen-printed on the position, where an external electrode 101 is to be formed, on the side faces of the sintered stack. Then, the sintered stack was fired at a temperature from 600 to 800° C. to form an external electrode, and thus a multi-layer piezoelectric device was obtained.

Lead wires were connected to external electrodes 101, and DC voltage of 3 KV/mm was applied to positive and negative external electrodes 101 via the lead wires for 15 minutes so as to apply polarization treatment, thereby to complete a piezoelectric actuator that employs a multi-layer piezoelectric device. DC voltage of 170 V was applied to the resultant multi-layer piezoelectric device and, as a result, all piezoelectric actuators except for sample No. 32 undergo displacement in the stacking direction. The piezoelectric actuator was continuously operated up to $1 \times 10^9$ times by applying AC voltage of 0 to +170 V at room temperature at a frequency of 150 Hz. The results are shown in Table 3. Table 3 is divided into Table 3(1) and Table 3(2).

TABLE 3(1)

| No. | Metal composition of second metallic paste layer (high-content metallic pate layer) | Metal composition of first metallic paste layer | Metal composition of second metal layer after firing | Void ratio of second metal layer after firing (%) | Metal composition of first metal layer after firing | Void ratio of first metal layer after firing (%) | Amount of displacement at initial state (μm) | Noise of harmonic components |
|---|---|---|---|---|---|---|---|---|
| 1 | 100% Ag | 100% Ag | 100% Ag | 25 | 100% Ag | 25 | 5 | generated |
| 2 | 100% Ag | 99% Ag—1% Pd | 100% Ag | 70 | 99.5% Ag—0.5% Pd | 15 | 10 | not generated |
| 3 | 100% Ag | 98% Ag—2% Pd | 99% Ag—1% PD | 80 | 99% Ag—1% Pd | 15 | 10 | not generated |
| 4 | 100% Ag | 95% Ag—5% Pd | 97% Ag—3% Pd | 85 | 96% Ag—4% Pd | 10 | 10 | not generated |
| 5 | 100% Ag | 90% Ag—10% Pd | 95% Ag—5% Pd | 75 | 90% Ag—10% Pd | 15 | 10 | not generated |
| 6 | 100% Ag | 80% Ag—20% Pd | 90% Ag—10% Pd | 65 | 85% Ag—15% Pd | 20 | 10 | not generated |
| 7 | 100% Ag | 70% Ag—30% Pd | 85% Ag—15% Pd | 60 | 75% Ag—25% Pd | 20 | 10 | not generated |
| 8 | 100% Ag | 98% Ag—2% Pt | 99% Ag—1% Pt | 80 | 99% Ag—1% Pt | 15 | 10 | not generated |
| 9 | 100% Ag | 97% Ag—3% Pt | 97% Ag—3% Pt | 85 | 97% Ag—3% Pt | 10 | 10 | not generated |
| 10 | 100% Ag | 95% Ag—5% Pt | 97% Ag—3% Pt | 85 | 96% Ag—4% Pt | 10 | 10 | not generated |
| 11 | 100% Ag | 90% Ag—10% Pt | 95% Ag—5% Pt | 75 | 90% Ag—10% Pt | 15 | 10 | not generated |
| 12 | 100% Ag | 80% Ag—20% Pt | 90% Ag—10% Pt | 65 | 85% Ag—15% Pt | 20 | 10 | not generated |
| 13 | 100% Ag | 70% Ag—30% Pt | 85% Ag—15% Pt | 60 | 75% Ag—25% Pt | 20 | 10 | not generated |
| 14 | 97% Ag—3% Pd | 95% Ag—5% Pd | 96% Ag—4% Pd | 75 | 96% Ag—4% Pt | 10 | 10 | not generated |
| 15 | 98% Ag—2% Pd | 95% Ag—5% Pd | 95% Ag—5% Pd | 85 | 95% Ag—5% Pt | 10 | 10 | not generated |
| 16 | 95% Ag—5% Pd | 90% Ag—10% Pd | 92% Ag—8% Pd | 80 | 91% Ag—9% Pd | 15 | 10 | not generated |
| 17 | 95% Ag—5% Pd | 85% Ag—15% Pd | 90% Ag—10% Pd | 75 | 86% Ag—14% Pd | 15 | 10 | not generated |
| 18 | 95% Ag—5% Pd | 75% Ag—25% Pd | 85% Ag—15% Pd | 65 | 80% Ag—20% Pd | 20 | 10 | not generated |
| 19 | 95% Ag—5% Pd | 65% Ag—35% Pd | 75% Ag—25% Pd | 60 | 70% Ag—30% Pd | 20 | 10 | not generated |

| No. | Beat sound at 1 kHz or more | Amount of displacement after $1 \times 10^9$ cycles (μm) | Peeling at stacked portion after continuous operation ($1 \times 10^9$ times) |
|---|---|---|---|
| 1 | generated | Cracks occurred | occurred |
| 2 | not generated | 9.5 | not occurred |
| 3 | not generated | 9.9 | not occurred |
| 4 | not generated | 10 | not occurred |
| 5 | not generated | 9.9 | not occurred |
| 6 | not generated | 9 | not occurred |
| 7 | not generated | 8 | not occurred |
| 8 | not generated | 9.9 | not occurred |
| 9 | not generated | 10 | not occurred |
| 10 | not generated | 10 | not occurred |
| 11 | not generated | 9.9 | not occurred |
| 12 | not generated | 9 | not occurred |
| 13 | not generated | 8 | not occurred |
| 14 | not generated | 9.9 | not occurred |
| 15 | not generated | 10 | not occurred |
| 16 | not generated | 10 | not occurred |
| 17 | not generated | 9.9 | not occurred |
| 18 | not generated | 9 | not occurred |
| 19 | not generated | 8 | not occurred |

TABLE 3(2)

| No. | Metal composition of second metallic paste layer (high-content metallic pate layer) | Metal composition of first metallic paste layer | Metal composition of second metal layer after firing | Void ratio of second metal layer after firing (%) | Metal composition of first metal layer after firing | Void ratio of first metal layer after firing (%) | Amount of displacement at initial state (μm) | Noise of harmonic components |
|---|---|---|---|---|---|---|---|---|
| 20 | 97% Ag—3% Pt | 95% Ag—5% Pt | 96% Ag—4% Pt | 75 | 96% Ag—4% Pt | 10 | 10 | not generated |
| 21 | 98% Ag—2% Pt | 95% Ag—5% Pt | 95% Ag—5% Pt | 85 | 95% Ag—5% Pt | 10 | 10 | not generated |
| 22 | 95% Ag—5% Pt | 90% Ag—10% Pt | 92% Ag—8% Pt | 80 | 91% Ag—9% Pt | 15 | 10 | not generated |
| 23 | 95% Ag—5% Pt | 85% Ag—15% Pt | 90% Ag—10% Pt | 75 | 86% Ag—14% Pt | 15 | 10 | not generated |
| 24 | 95% Ag—5% Pt | 75% Ag—25% Pt | 85% Ag—15% Pt | 65 | 80% Ag—20% Pt | 20 | 10 | not generated |
| 25 | 95% Ag—5% Pt | 65% Ag—35% Pt | 75% Ag—25% Pt | 60 | 70% Ag—30% Pt | 20 | 10 | not generated |
| 26 | 97% Ag—3% Pt | 95% Ag—5% Pd | 96% Ag—4% Pt | 75 | 96% Ag—4% Pd | 10 | 10 | not generated |
| 27 | 98% Ag—2% Pt | 95% Ag—5% Pd | 95% Ag—5% Pt | 85 | 95% Ag—5% Pd | 10 | 10 | not generated |
| 28 | 95% Ag—5% Pt | 90% Ag—10% Pd | 92% Ag—8% Pt | 80 | 91% Ag—9% Pd | 15 | 10 | not generated |
| 29 | 95% Ag—5% Pt | 85% Ag—15% Pd | 90% Ag—10% Pt | 75 | 86% Ag—14% Pd | 15 | 10 | not generated |
| 30 | 95% Ag—5% Pt | 75% Ag—25% Pd | 85% Ag—15% Pt | 65 | 80% Ag—20% Pd | 20 | 10 | not generated |
| 31 | 95% Ag—5% Pt | 65% Ag—35% Pd | 75% Ag—25% Pt | 60 | 70% Ag—30% Pd | 20 | 10 | not generated |
| 32 | 100% Pt + acryl beads | 100% Pt + acryl beads | 100% Pt | 60 | 100% Pt | 60 | 0 | not generated |
| 33 | Sputtering method 70% Ag—30% Pd | Sputtering method 70% Ag—30% Pd | 70% Ag—30% Pd | 10 | 70% Ag—30% Pd | 10 | 5 | not generated |

TABLE 3(2)-continued

| No. | Beat sound at 1 kHz or more | Amount of displacement after $1 \times 10^9$ cycles (μm) | Peeling at stacked portion after continuous operation ($1 \times 10^9$ times) |
|---|---|---|---|
| 20 | not generated | 9.9 | not occurred |
| 21 | not generated | 10 | not occurred |
| 22 | not generated | 10 | not occurred |
| 23 | not generated | 9.9 | not occurred |
| 24 | not generated | 9 | not occurred |
| 25 | not generated | 8 | not occurred |
| 26 | not generated | 9.9 | not occurred |
| 27 | not generated | 10 | not occurred |
| 28 | not generated | 10 | not occurred |
| 29 | not generated | 9.9 | not occurred |
| 30 | not generated | 9 | not occurred |
| 31 | not generated | 8 | not occurred |
| 32 | not generated | not occurred | not occurred |
| 33 | generated | cracks occurred | occurred |

As is apparent from the results in Table 3, in samples Nos. 1 and 33 as Comparative Examples, peeling occurred in the interface between the stacks. It was found that, when the frequency of the drive voltage is gradually increased from 150 Hz so as to confirm rapid response of a piezoelectric actuator, beat sound is generated by the device at 1 kHz or more (beat sound could be heard with the ears).

When the pulse waveform was confirmed by an oscilloscope DL1640L manufactured by Yokogawa Electric Corporation so as to confirm the frequency of the drive voltage in the device where beat sound is generated, harmonic noise could be confirmed at the position corresponding to frequencies integer times the frequency of the drive voltage. In sample No. 32, since displacement and deformation of a piezoelectric material was absorbed as a result of deformation of a metal layer by the cushion effect of the metal layer, the entire device caused no deformation.

In samples Nos. 2 to 31 as Examples of the present invention, an amount of displacement of the device did not drastically decrease even after the continuous operation $1 \times 10^9$ times and samples had an effective amount of displacement required as a piezoelectric actuator.

Samples show excellent durability when a mass percentage X of silver of a metallic paste layer is 85% or more and a difference in the mass percentage of the metallic paste layer is 2% or more and 10% or less. Samples Nos. 4, 9, 10, 15, 16, 21, 22, 27 and 28, in which a mass percentage X of silver of the metallic paste layer is 90% or more and a difference in the mass percentage is 3% or more and 5% or less, showed most excellent durability. The lump-containing layer of these samples was constituted from plural metal lumps that are separated from by voids.

Example 4

Multi-Layer Piezoelectric Device

A multi-layer piezoelectric device was manufactured as follows. First, a raw powder consisting mainly of a lead titanate zirconate (PZT) powder having a mean particle size of 0.4 μm, a binder, and a plasticizer were mixed to prepare a slurry. The slurry was formed into a ceramic green sheet having a thickness of 150 μm by a doctor blade method. On one surface of the ceramic green sheet, an electrically conductive paste prepared by adding a binder to a raw powder such as a silver alloy powder with the composition shown in Table 4 was printed in a thickness of 30 μm using a screen printing method.

Figure 26:
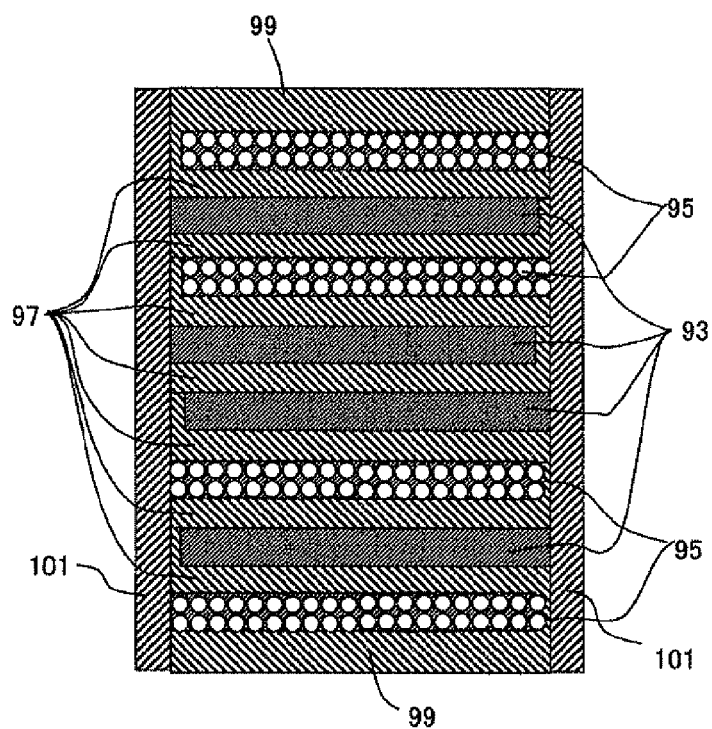
FIG. 26 is a sectional view showing a multi-layer piezoelectric device according to further another embodiment of the present invention.

Then, green sheets were stacked to obtain a stacked compact having a shape shown in FIG. 26. Among plural metal layers, a low-content metallic paste is formed at the second position from both ends in the stacking direction. 100 metal layers were stacked. Regarding the position where a predetermined thickness of a ceramic layer is required, a required number of only green sheets were stacked without printing the electrically conductive paste.

In the same manner as described above, the stacked compact was treated to remove the binder and the stacked compact was fired to obtain a sintered stack. Therefore, silver diffused from the metal layer having a high concentration to the metal layer having a low concentration to form a porous metal layer 95 having a high void ratio, and thus comparatively dense metal layer 93 was formed. In the same manner as in Example 3, an external electrode was formed to obtain a multi-layer piezoelectric device. In the same manner as in Example 3, lead wires were connected to external electrodes 101, and DC voltage was applied so as to apply polarization treatment, thereby to complete a piezoelectric actuator. As a result, all piezoelectric actuators undergo displacement in the stacking direction. The piezoelectric actuator was continuously operated up to $1 \times 10^9$ times by applying AC voltage of 0 to +170 V at room temperature at a frequency of ISO Hz. The results are shown in Table 4.

TABLE 4

| No. | Metal composition of second metallic paste layer (metal composition of metallic paste layer of both sides of low-content metallic pate layer) | Metal composition of first metallic paste layer (low-content metallic pate layer) | Metal composition of second metal layer after firing | Void ratio of second metal layer after firing (%) | Metal composition of first metal layer after firing | Void ratio of first metal layer after firing (%) | Amount of displacement at initial state (μm) | Noise of harmonic components |
|---|---|---|---|---|---|---|---|---|
| 1 | 100% Ag | 100% Ag | 100% Ag | 25 | 100% Ag | 25 | 5 | generated |
| 2 | 100% Ag | 99% Ag—1% Pd | 100% Ag | 55 | 99.5% Ag—0.5% Pd | 15 | 10 | not generated |

TABLE 4-continued

| No. | | | | | | | | |
|---|---|---|---|---|---|---|---|---|
| 3 | 97% Ag—3% Pd | 95% Ag—5% Pd | 96% Ag—4% PD | 60 | 96% Ag—4% Pd | 15 | 10 | not generated |
| 4 | 98% Ag—2% Pd | 95% Ag—5% Pd | 97% Ag—3% Pd | 65 | 97% Ag—3% Pd | 15 | 10 | not generated |
| 5 | 95% Ag—5% Pd | 90% Ag—10% Pd | 92% Ag—8% Pd | 70 | 92% Ag—8% Pd | 15 | 10 | not generated |
| 6 | 95% Ag—5% Pd | 85% Ag—15% Pd | 90% Ag—10% Pd | 75 | 90% Ag—10% Pd | 10 | 10 | not generated |
| 7 | 95% Ag—5% Pd | 80% Ag—20% Pd | 90% Ag—10% Pd | 75 | 85% Ag—15% Pd | 10 | 10 | not generated |
| 8 | 95% Ag—5% Pd | 75% Ag—25% Pd | 85% Ag—15% Pd | 80 | 80% Ag—20% Pt | 10 | 10 | not generated |
| 9 | 95% Ag—5% Pd | 70% Ag—30% Pd | 85% Ag—15% Pd | 80 | 80% Ag—20% Pt | 10 | 10 | not generated |
| 10 | 95% Ag—5% Pd | 65% Ag—35% Pd | 75% Ag—25% Pd | 60 | 70% Ag—30% Pt | 20 | 10 | not generated |
| 11 | 100% Ag | 80% Ag—20% Pd | 90% Ag—10% Pd | 80 | 85% Ag—15% Pt | 10 | 10 | not generated |
| 12 | 100% Ag | 80% Ag—20% Pt | 90% Ag—10% Pt | 80 | 85% Ag—15% Pt | 10 | 10 | not generated |
| 13 | 95% Ag—5% Pt | 75% Ag—25% Pt | 85% Ag—15% Pt | 80 | 80% Ag—20% Pt | 10 | 10 | not generated |
| 14 | 95% Ag—5% Pt | 75% Ag—25% Pd | 85% Ag—15% Pt | 80 | 80% Ag—20% Pd | 10 | 10 | not generated |

| No. | Beat sound at 1 kHz or more | Amount of displacement after $1 \times 10^9$ cycles (μm) | Peeling at stacked portion after continuous operation ($1 \times 10^9$ times) |
|---|---|---|---|
| 1 | generated | Cracks occurred | occurred |
| 2 | not generated | 9.9 | not occurred |
| 3 | not generated | 9.9 | not occurred |
| 4 | not generated | 9.9 | not occurred |
| 5 | not generated | 9.9 | not occurred |
| 6 | not generated | 10 | not occurred |
| 7 | not generated | 10 | not occurred |
| 8 | not generated | 10 | not occurred |
| 9 | not generated | 10 | not occurred |
| 10 | not generated | 9.5 | not occurred |
| 11 | not generated | 10 | not occurred |
| 12 | not generated | 10 | not occurred |
| 13 | not generated | 10 | not occurred |
| 14 | not generated | 10 | not occurred |

As is apparent from the results in Table 4, in sample No. 1, peeling occurred in the interface between the stacks. It was found that, when the frequency of the drive voltage is gradually increased from 150 Hz so as to confirm rapid response of a piezoelectric actuator, beat sound is generated by the device at 1 kHz or more (beat sound could be heard with the ears). When the pulse waveform was confirmed by an oscilloscope DL1640L manufactured by Yokogawa Electric Corporation so as to confirm the frequency of the drive voltage in the device where beat sound is generated, harmonic noise could be confirmed at the position corresponding to frequencies integer times the frequency of the drive voltage.

In samples Nos. 2 to 14 as Examples of the present invention, an amount of displacement of the device did not drastically decrease even after the continuous operation $1\times10^9$ times and samples had an effective amount of displacement required as a piezoelectric actuator, and thus a piezoelectric actuator having excellent durability can be manufactured.

It was found as a result of taking notice of durability that a multi-layer piezoelectric device having a higher void ratio showed more excellent durability. When the difference of mass percentage is 3 or more and 25 or less, like samples Nos. 2 to 9 and 11 to 14, the resultant multi-layer piezoelectric devices are excellent because an amount of displacement of the device scarcely varies even after a cycling test.

In samples Nos. 6 to 9 and 11 to 14 in which the difference of the mass percentage is 10 or more and 25 or less, diffusion of silver properly occurred and the high-content metallic paste layer after firing was constituted from plural metal lumps that are separated by voids. These metal lumps are dispersed between ceramic layers in the state of being electrically insulated with each other. Therefore, the resulting layer having excellent insulating properties, that does not function as an electrode. Moreover, since plural metal lumps are dispersed between ceramic layers in a proper size and amount, it functioned as an excellent a stress relieving layer capable of preventing adjacent ceramic layers at both side from bonding with each other during firing.

Example 5

Multi-Layer Piezoelectric Device

A multi-layer piezoelectric device was manufactured as follows. First, a ceramic green sheet having a thickness of 150 μm was formed in the same manner as in Example 3. On one surface of the ceramic green sheet, an electrically conductive paste prepared by adding a binder to a raw powder such as a silver alloy powder with the composition shown in Table 5 was printed in a thickness of 30 μm using a screen printing method. Then, green sheets were stacked to obtain a stacked compact having a shape shown in FIG. 21, comprising 300 metal layers stacked. Regarding the position where a predetermined thickness of a ceramic layer is required, a required number of only green sheets were stacked without printing the electrically conductive paste.

After treating the stacked compact to remove the binder in the same manner as in Example 3, the stacked compact was fired to obtain a sintered stack. Therefore, when the metal layers with a difference in silver concentration are formed via a ceramic layer, silver diffused from the metal layer having a high concentration to the metal layer having a low concentration, and thus a metal layer formed by printing a high-content metal paste was converted into a porous metal layer 95 having a high void ratio, and thus comparatively dense metal layer 93 was formed.

In the same manner as in Example 3, a multi-layer piezoelectric device was manufactured and then subjected to a polarization treatment to complete a piezoelectric actuator. DC voltage of 170 V was applied to the resultant multi-layer piezoelectric device and, as a result, all piezoelectric actuators except for sample Nos. 32 undergo displacement in the stacking direction. The piezoelectric actuator was continuously operated up to $1\times10^9$ times by applying AC voltage of 0 to +170 V at room temperature at a frequency of 150 Hz. The results are shown in Table 5.

TABLE 5

| No. | Metal composition of first metallic paste layer (high-content metallic pate layer) | Printing position of second metallic paste layer (layer) | Metal composition of first metallic paste layer | Metal composition of second metal layer after firing | Void ratio of second metal layer after firing (%) | Metal composition of first metal layer after firing | Void ratio of first metal layer after firing (%) | Amount of displacement at initial state (μm) |
|---|---|---|---|---|---|---|---|---|
| 1 | 100% Ag | — | 100% Ag | 100% Ag | 25 | 100% Ag | 25 | 45 |
| 2 | 98% Ag—2% Pd | 50, 100, 200, 250 | 95% Ag—5% PD | 95% Ag—5% PD | 85 | 95% Ag—5% PD | 10 | 55 |
| 3 | 98% Ag—2% Pd | 50, 100, 150, 200, 250 | 95% Ag—5% PD | 95% Ag—5% PD | 85 | 95% Ag—5% PD | 10 | 60 |
| 4 | 98% Ag—2% Pd | 1, 50, 100, 150, 200, 250, 300 | 95% Ag—5% PD | 95% Ag—5% PD | 85 | 95% Ag—5% PD | 10 | 65 |

| No. | Noise of harmonic components | Beat sound at 1 kHz or more | Amount of displacement after $1 \times 10^9$ cycles (μm) | Peeling at stacked portion after continuous operation ($1 \times 10^9$ times) |
|---|---|---|---|---|
| 1 | generated | generated | Cracks occurred | occurred |
| 2 | not generated | not generated | 54.9 | not occurred |
| 3 | not generated | not generated | 59.9 | not occurred |
| 4 | not generated | not generated | 60 | not occurred |

As is apparent from the results in Table 5, in sample Nos. 1 as Comparative Example, peeling occurred in the interface between the stacks. It was found that, when the frequency of the drive voltage is gradually increased from 150 Hz so as to confirm rapid response of a piezoelectric actuator, beat sound is generated by the device at 1 kHz or more (beat sound could be heard with the ears). When the pulse waveform was confirmed by an oscilloscope DL1640L manufactured by Yokogawa Electric Corporation so as to confirm the frequency of the drive voltage in the device where beat sound is generated, harmonic noise could be confirmed at the position corresponding to frequencies integer times the frequency of the drive voltage.

In samples Nos. 2 to 4 as Examples of the present invention, an amount of displacement of the device did not drastically decrease even after the continuous operation $1 \times 10^9$ times and samples had an effective amount of displacement required as a piezoelectric actuator, and thus a piezoelectric actuator having excellent durability could be manufactured.

Example 6

Multi-Layer Piezoelectric Device

A multi-layer piezoelectric device was manufactured as follows. First, a ceramic green sheet having a thickness of 150 μm was formed in the same manner as in Example 3. On one surface of the ceramic green sheet, an electrically conductive paste prepared by adding a binder to a raw powder such as a silver alloy powder with the composition shown in Table 6 was printed in a thickness of 30 μm using a screen printing method. Then, green sheets were stacked to obtain a stacked compact having a shape shown in FIG. 24, comprising 200 metal layers stacked. Regarding the position where a predetermined thickness of a ceramic layer is required, a required number of only green sheets were stacked without printing the electrically conductive paste.

At this time, at the stacked position shown in Table 6, a high-content metal paste was printed so that plural metal lumps 103 are scattered in the periphery 131 while being separated with each other after firing, as shown in FIG. 24 (b), using a screen print making comprising with a mask pattern having a shape of the periphery 131.

In the same manner as in Example 3, the stacked compact was treated to remove the binder and the stacked compact was fired to obtain a sintered stack. Therefore, silver diffuses from the region of the high-content metal paste printed on the periphery 131 to the metallic paste layer having a low silver concentration, that adjoins therewith in the stacking direction. After firing, plural metal lumps 103 were dispersed while separating with each other at the periphery 131. On the other metal layer, comparatively dense metal layer 93 was formed.

In the same manner as in Example 3, a multi-layer piezoelectric device was manufactured and then subjected to a polarization treatment to complete a piezoelectric actuator. DC voltage of 170 V was applied to the resultant multi-layer piezoelectric device and, as a result, all piezoelectric actuators undergo displacement in the stacking direction. The piezoelectric actuator was continuously operated up to $1 \times 10^9$ times by applying AC voltage of 0 to +170 V at room temperature at a frequency of 150 Hz. The results are shown in Table 6.

TABLE 6

| No. | Metal composition of first metallic paste layer (high-content metallic pate layer) | Printing position of second metallic paste layer (layer) | Metal composition of first metallic paste layer | Metal composition of second metal layer after firing | Void ratio of second metal layer after firing (%) | Metal composition of first metal layer after firing | Void ratio of first metal layer after firing (%) | Amount of displacement at initial state (μm) |
|---|---|---|---|---|---|---|---|---|
| 1 | 100% Ag | — | 100% Ag | 100% Ag | 25 | 100% Ag | 25 | 30 |
| 2 | 98% Ag—2% Pd | 50, 150 | 95% Ag—5% PD | 95% Ag—5% PD | 85 | 95% Ag—5% PD | 10 | 37 |
| 3 | 98% Ag—2% Pd | 50, 100, 150 | 95% Ag—5% PD | 95% Ag—5% PD | 85 | 95% Ag—5% PD | 10 | 40 |
| 4 | 98% Ag—2% Pd | 1, 50, 100, 150, 200 | 95% Ag—5% PD | 95% Ag—5% PD | 85 | 95% Ag—5% PD | 10 | 40 |

TABLE 6-continued

| No. | Noise of harmonic components | Beat sound at 1 kHz or more | Amount of displacement after $1 \times 10^9$ cycles (μm) | Peeling at stacked portion after continuous operation ($1 \times 10^9$ times) |
|---|---|---|---|---|
| 1 | generated | generated | Cracks occurred | occurred |
| 2 | not generated | not generated | 39.9 | not occurred |
| 3 | not generated | not generated | 39.9 | not occurred |
| 4 | not generated | not generated | 40 | not occurred |

As is apparent from the results in Table 6, in sample No. 1 as Comparative Example, peeling occurred in the interface between the stacks. It was found that, when the frequency of the drive voltage is gradually increased from 150 Hz so as to confirm rapid response of a piezoelectric actuator, beat sound is generated by the device at 1 kHz or more (beat sound could be heard with the ears). When the pulse waveform was confirmed by an oscilloscope DL1640L manufactured by Yokogawa Electric Corporation so as to confirm the frequency of the drive voltage in the device where beat sound is generated, harmonic noise could be confirmed at the position corresponding to frequencies integer times the frequency of the drive voltage.

In samples Nos. 2 to 4 as Examples of the present invention, an amount of displacement of the device did not drastically decrease even after the continuous operation $1 \times 10^9$ times and samples had an effective amount of displacement required as a piezoelectric actuator, and thus a piezoelectric actuator having excellent durability can be manufactured.

The invention claimed is:

1. A method for manufacturing a ceramic member comprising:
    a step of forming a stacked compact from a plurality of metallic paste layers containing Ag that are stacked one on another via ceramic green sheets, and
    a step of firing the stacked compact, wherein, when a mass percentage X is a proportion of Ag to a total metal content in the metallic paste layers, at least one of said plurality of metallic paste layers is formed as a second metallic paste layer that contains Ag so that the mass percentage X is higher than that of a first metallic paste layer which is a metallic paste layer that contains Pd or Pt in addition to a main component Ag and that adjoins the second metallic paste layer in a stacking direction in the step of forming the stacked compact, and
    wherein a void ratio of a second metal layer formed by firing the second metallic paste layer is larger than a void ratio of a first metal layer formed by firing the first metallic paste layer.

2. The method for manufacturing a ceramic member according to claim 1, wherein the mass percentage X of the second metallic paste layer is set higher than those of the first metallic paste layers that adjoin on both sides of the second metallic paste layer in the stacking direction.

3. The method for manufacturing a ceramic member according to claim 1, wherein a mass percentage XH which is the mass percentage X of the second metallic paste layer and a mass percentage XL which is the mass percentage X of the first metallic paste layer adjacent to the second metallic paste layer in the stacking direction are set so as to satisfy $XL+0.1 \leq XH \leq XL+30$.

4. The method for manufacturing a ceramic member according to claim 1, wherein the mass percentages X of said plurality of metallic paste layers are set so as to satisfy $85 \leq X \leq 100$.

5. The method for manufacturing a ceramic member according to claim 1, wherein a plurality of said second metallic paste layers are disposed in the step of forming a stacked compact.

6. The method for manufacturing a ceramic member according to claim 5, wherein said plurality of second metallic paste layers are disposed so that a plurality of metal layers other than the second metallic paste layers are interposed between the second metallic paste layers.

7. The method for manufacturing a ceramic member according to claim 5, wherein said plurality of second metallic paste layers are disposed in accordance with a predetermined rule in the stacking direction of the stacked compact.

8. The method for manufacturing a ceramic member according to claim 5, wherein the second metallic paste layers and metal layers other than the second metallic paste layers are alternately disposed.

9. A method for manufacturing a ceramic member comprising:
    a step of forming a stacked compact from a plurality of metallic paste layers containing Ag that are stacked one on another via ceramic green sheets, and
    a step of firing the stacked compact, wherein, when a mass percentage X is a proportion of Ag to a total metal content in the metallic paste layers, at least one of said plurality of metallic paste layers is formed as a first metallic paste layer that contains Pd or Pt in addition to a main component Ag so that the mass percentage X is lower than those of a second metallic paste layers containing Ag which are metallic paste layers that adjoin on both sides of the first metallic paste layer in a stacking direction,
    wherein a void ratio of a second metal layer formed by firing the second metallic paste layer is larger than a void ratio of a first metal layer formed by firing the first metallic paste layer.

10. The method for manufacturing a ceramic member according to claim 9, wherein a mass percentage XL which is the mass percentage X of the first metallic paste layer and a mass percentage XH which is the mass percentage X of the second metallic paste layer adjacent to the first metallic paste layer in the stacking direction are set so as to satisfy $XL-0.1 \leq XH \leq XL-30$.

11. The method for manufacturing a ceramic member according to claim 9, wherein the mass percentages X of said plurality of metallic paste layers are set so as to satisfy $85 \leq X \leq 100$.

12. The method for manufacturing a ceramic member according to claim 9, wherein a plurality of said first metallic paste layers are disposed in the step of forming a stacked compact.

13. The method for manufacturing a ceramic member according to claim 12, wherein said plurality of first metallic paste layers are disposed so that a plurality of metallic paste layers other than the first metallic paste layers are interposed between the first metallic paste layers.

14. The method for manufacturing a ceramic member according to claim 13, wherein said plurality of first metallic paste layers are disposed in accordance with a predetermined rule in the stacking direction of the stacked compact.

15. The method for manufacturing a ceramic member according to claim 13, wherein the first metallic paste layers and metallic past layers other than the first metallic paste layers are alternately disposed.

16. A method for manufacturing a ceramic member comprising:
   a step of forming a stacked compact from a plurality of metallic paste layers containing Ag that are stacked one on another via ceramic green sheets, and
   a step of firing the stacked compact,
wherein, when a mass percentage X is a proportion of Ag a total metal content in the metallic paste layers, the mass percentage X of a portion containing Ag of at least one of said plurality of metallic paste layers is set higher than that of a metallic paste layer that contains Pd or Pt in addition to a main component Ag and that adjoins said portion in a stacking direction, and
   wherein a void ratio of the portion is larger than a void ratio of a metal layer formed by firing the metallic paste layer that adjoins in the stacking direction.

17. The method for manufacturing a ceramic member according to claim 16, wherein the mass percentage X of the portion is set higher than metallic paste layers when adjoined on both sides of said portion in the stacking direction.

18. The method for manufacturing a ceramic member according to claim 16, wherein the mass percentage X of a region other than said portion is set the same as that of the metallic paste layer that adjoins said portion in the stacking direction.

* * * * *